US010370656B2

(12) United States Patent
Mirkin et al.

(10) Patent No.: US 10,370,656 B2
(45) Date of Patent: Aug. 6, 2019

(54) NUCLEIC ACID FUNCTIONALIZED NANOPARTICLES FOR THERAPEUTIC APPLICATIONS

(71) Applicant: NORTHWESTERN UNIVERSITY, Evanston, IL (US)

(72) Inventors: Chad A. Mirkin, Wilmette, IL (US); David A. Giljohann, Chicago, IL (US); Dwight S. Seferos, Toronto (CA)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/296,387

(22) Filed: Oct. 18, 2016

(65) Prior Publication Data

US 2017/0137809 A1 May 18, 2017

Related U.S. Application Data

(63) Continuation of application No. 12/130,643, filed on May 30, 2008, now Pat. No. 9,506,056, which is a continuation-in-part of application No. PCT/US2006/022325, filed on Jun. 8, 2006.

(60) Provisional application No. 60/985,462, filed on Nov. 5, 2007, provisional application No. 60/940,886, filed on May 30, 2007.

(51) Int. Cl.
| | | |
|---|---|---|
| *C12N 15/113* | (2010.01) | |
| *A61K 31/7088* | (2006.01) | |
| *A61K 9/51* | (2006.01) | |
| *C12N 15/11* | (2006.01) | |
| *C12N 15/87* | (2006.01) | |

(52) U.S. Cl.
CPC .............. *C12N 15/113* (2013.01); *A61K 9/51* (2013.01); *A61K 31/7088* (2013.01); *C12N 15/111* (2013.01); *C12N 15/87* (2013.01); *C12N 2310/11* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |

(Continued)

FOREIGN PATENT DOCUMENTS

| | | |
|---|---|---|
| EP | 1072679 A2 | 1/2001 |
| EP | 1674128 A1 | 6/2006 |

(Continued)

OTHER PUBLICATIONS

Weissleder (2005) "Cell-specific targeting of nanoparticles by multivalent attachment of small molecules", Nature Biotechnology, 23(11): 1418-23.*
Van de Donk, et al. (2003) "Chemosenitization of myeloma plasma cells by an antisense-mediated downregulation of Bcl-2 protein", Leukemia, 17: 211-19.*
Fahmy, et al. (2005) "Targeted for drug delivery", Materials Today, 8(8 Supp.): 18-26.*
Agasti et al., Photoregulated release of caged anticancer drugs from gold nanoparticles, J. Am. Chem. Soc., 131(16):5728-9 (2009).
Agrawal et al., Antisence therapeutics: Is it as simple as complementary base recognition? *Mol. Med. Today*, 6: 72-81 (2000).

(Continued)

*Primary Examiner* — Robert M Kelly
(74) *Attorney, Agent, or Firm* — Marshall, Gerstein & Borun LLP

(57) ABSTRACT

Materials and methods for modulating cellular uptake of functionalized nanoparticles are provided. Also provided are materials and methods for modulating the effectiveness of a therapeutic agent with a functionalized nanoparticle.

16 Claims, 3 Drawing Sheets

(56) References Cited

U.S. PATENT DOCUMENTS

| | | |
|---|---|---|
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,654 A | 11/1993 | Kreft et al. |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,506,564 B1 | 1/2003 | Mirkin et al. |
| 6,544,776 B1 | 4/2003 | Gold et al. |
| 6,656,730 B1 | 12/2003 | Manoharan |
| 6,677,153 B2 | 1/2004 | Iversen |
| 6,709,825 B2 | 3/2004 | Mirkin et al. |
| 6,750,016 B2 | 6/2004 | Mirkin et al. |
| 6,767,702 B2 | 7/2004 | Mirkin et al. |
| 6,844,161 B2 | 1/2005 | Siani et al. |
| 6,991,900 B2 | 1/2006 | Shizuya |
| 7,098,320 B1 | 8/2006 | Mirkin et al. |
| 7,223,833 B1 | 5/2007 | Nielsen et al. |
| 7,238,472 B2 | 7/2007 | Mirkin et al. |
| 7,332,586 B2 | 2/2008 | Franzen et al. |

(56) References Cited

U.S. PATENT DOCUMENTS

| | | | |
|---|---|---|---|
| 7,727,969 B2* | 6/2010 | Farokhzad | A61K 48/0041 424/486 |
| 2002/0172953 A1 | 11/2002 | Mirkin et al. | |
| 2003/0147966 A1 | 8/2003 | Franzen et al. | |
| 2003/0181412 A1 | 9/2003 | Erikson | |
| 2004/0219565 A1 | 11/2004 | Kauppinen et al. | |
| 2004/0247680 A1* | 12/2004 | Farokhzad | A61K 48/0041 424/486 |
| 2004/0248099 A1 | 12/2004 | Goppelt et al. | |
| 2005/0059016 A1 | 3/2005 | Ecker et al. | |
| 2005/0074753 A1 | 4/2005 | Goldsborough | |
| 2005/0096263 A1 | 5/2005 | Keay et al. | |
| 2005/0136258 A1 | 6/2005 | Nie et al. | |
| 2005/0197315 A1 | 9/2005 | Taira et al. | |
| 2005/0214782 A1 | 9/2005 | Chen et al. | |
| 2005/0244858 A1 | 11/2005 | Rossi et al. | |
| 2006/0008907 A1 | 1/2006 | Friedman et al. | |
| 2006/0019917 A1 | 1/2006 | Guerciolini et al. | |
| 2006/0025363 A1 | 2/2006 | Breitenbach et al. | |
| 2006/0035344 A1 | 2/2006 | Pachuk et al. | |
| 2006/0105343 A1 | 5/2006 | Zetter et al. | |
| 2006/0159921 A1 | 7/2006 | Murthy et al. | |
| 2006/0183247 A1 | 8/2006 | Kim et al. | |
| 2006/0188560 A1 | 8/2006 | Cheresh et al. | |
| 2006/0233712 A1 | 10/2006 | Penades et al. | |
| 2006/0252037 A1 | 11/2006 | Kolesnick et al. | |
| 2006/0275371 A1 | 12/2006 | Dai et al. | |
| 2007/0105139 A1 | 5/2007 | Nishigaki et al. | |
| 2007/0190160 A1 | 8/2007 | Turos et al. | |
| 2008/0194463 A1 | 8/2008 | Weller et al. | |
| 2008/0213177 A1 | 9/2008 | Rademacher et al. | |
| 2008/0220072 A1 | 9/2008 | Unger et al. | |
| 2008/0279946 A1 | 11/2008 | Hainfeld | |
| 2008/0305106 A1 | 12/2008 | Brennan et al. | |
| 2008/0306016 A1 | 12/2008 | Mirkin et al. | |
| 2008/0317749 A1 | 12/2008 | Kastelein et al. | |
| 2008/0317768 A1 | 12/2008 | Bianchi | |
| 2009/0035576 A1 | 2/2009 | Prasad et al. | |
| 2009/0081244 A1 | 3/2009 | Glenn et al. | |
| 2009/0209629 A1 | 8/2009 | Mirkin et al. | |
| 2009/0286853 A1 | 11/2009 | Gryaznov et al. | |
| 2010/0183634 A1 | 7/2010 | Luo et al. | |
| 2011/0172404 A1 | 7/2011 | Luo et al. | |
| 2011/0262976 A1 | 10/2011 | Kandula et al. | |

FOREIGN PATENT DOCUMENTS

| | | |
|---|---|---|
| WO | WO-1989/02439 A1 | 3/1989 |
| WO | WO-1993/007883 | 4/1993 |
| WO | WO-1993/21259 | 10/1993 |
| WO | WO-1995/06731 | 3/1995 |
| WO | WO-1995/11910 | 5/1995 |
| WO | WO-1997/012896 A1 | 4/1997 |
| WO | WO-1998/004740 A1 | 2/1998 |
| WO | WO-1998/39352 A1 | 9/1998 |
| WO | WO-1998/047343 | 10/1998 |
| WO | WO-1999/011655 | 3/1999 |
| WO | WO-1999/014226 A2 | 3/1999 |
| WO | WO-2000/043045 A1 | 7/2000 |
| WO | WO-2001/000876 A1 | 1/2001 |
| WO | WO-2001/049869 | 7/2001 |
| WO | WO-2001/051665 A2 | 7/2001 |
| WO | WO-2001/073123 A2 | 10/2001 |
| WO | WO-2002/44321 A2 | 6/2002 |
| WO | WO-2002/096262 A2 | 12/2002 |
| WO | WO-2003/008539 A2 | 1/2003 |
| WO | WO-2003/051278 A2 | 6/2003 |
| WO | WO-2005/116226 A2 | 12/2005 |
| WO | WO-2006/012695 A1 | 2/2006 |
| WO | WO-2006/045541 A1 | 5/2006 |
| WO | WO-2006/138145 A1 | 12/2006 |
| WO | WO-2008/141289 A1 | 11/2008 |
| WO | WO-2008/151049 A2 | 12/2008 |
| WO | WO-2010/060110 A1 | 5/2010 |

OTHER PUBLICATIONS

Ahmadi et al., "Shape-controlled synthesis of colloidal platinum nanoparticles," Science. 272: 1924-6 (1996).

Aime et al., Insights into the use of paramagnetic Gd(III) complexes in MR-molecular imaging investigations, J. Magn. Reson. Imaging, 16(4):394-406 (2002).

Aime et al., Pushing the sensitivity envelope of lanthanide-based magnetic resonance imaging (MRI) contrast agents for molecular imaging applications, Acc. Chem. Res., 42(7):822-31 (2009).

Alivisatos et al., Organization of 'nanocrystal molecules' using DNA. Nature, 382: 609-11 (1996).

Allara et al., "Spontaneously organized molecular assemblies. 1. Formation, dynamics, and physical properties of n-alkanoic acids absorbed from solution on an oxidized alumnium surface," Langmuir. 1:45-52 (1985).

Allara et al., "The study of the gas-solid interaction of acetic acid with a cuprous oxide surface using reflection-absorption spectroscopy," J. Colloid Interface Sci. 49: 410-21 (1974).

Alric et al., Gadolinium chelate coated gold nanoparticles as contrast agents for both X-ray computed tomography and magnetic resonance imaging, J. Am. Chem. Soc., 130(18):5908-15 (2008).

Altieri, Survivin, versatile modulation of cell division and apoptosis in cancer, Oncogene, 22: 8581-9 (2003).

Altschul et al., "Basic local alignment search tool," J. Mol. Biol. 215: 403-10 (1990).

Amirkhanov et al., Design of (Gd-DO3A)n-polydiamidopropanoyl-peptide nucleic acid-D(Cys-Ser-Lys-Cys) magnetic resonance contrast agents. *Biopolymers*, 89(12): 1061-76 (2008).

Aynie, et al., Spongelike alginate nanoparticles as a new potential system for the delivery of antisense oligonucleotides. Antisense Nucl. Acid Drug Dev., 9: 301-12 (1999).

Bahnemann, Photochemical Conversion and Storage of Solar Energy, Kluwer Academic Publishers 251-276 (1991).

Baker et al., Dendrimer-mediated cell transfection in vitro. Meth. Molec. Biol., 245: 67-81 (2004).

Bath et al., DNA nanomachines, Nat. Nanotechnol., 2: 275-84 (2007).

Baudhuin et al., Molecular interactions between colloidal gold, proteins, and living cells. Chapter 1, pp. 1-17 (1989).

Berton, et al., Highly loaded nanoparticulate carrier using an hydrophobic antisense oligonucleotide complex, Eur. J. Pharma. Sci., 9: 163-70 (1999).

Besch et al., Characterization and quantification of triple helix formation in chromosomal DNA. *J. Mol. Biol.*, 341: 979-89 (2004).

Bharali et al., "Organically modified silica nanoparticles: a nonviral vector for in vivo gene delivery and expression in the brain," Proc. Natl. Acad. Sci. USA. 102:11539-44 (2005).

Biancone et al., Magnetic resonance imaging of gadolinium-labeled pancreatic islets for experimental transplantation, NMR Biomed., 20(1):40-8 (2007).

Bielinska et al., "DNA complexing with polyamidoamine dendrimers: implications for transfection," *Bioconjugate Chem.* 10:843-50 (1999).

Birck et al., Mutation and allelic loss of the PTEN/MMAC1 gene in primary and metastatic melanoma biopsies, J. Invest. Dermatol., 114: 277-80 (2000).

Bowman et al., Inhibition of HIV fusion with multivalent gold nanoparticles, J. Am. Chem. Soc., 130(22):6896-7 (2008).

Bramhill, Bacterial cell division, *Annu. Rev. Cell Dev. Biol.*, 13: 395-424 (1997).

Bratu et al., Visualizing the distribution and transport of mRNAs in living cells, Proc. Natl. Acad. Sci. USA, 100: 13308-13 (2003).

Brus, "Quantum crystallites and nonlinear optics," *Appl. Phys. A.* 53: 465-74 (1991).

Burwell, "Modified silica gels as absorbents and catalysts," *Chemical Technology*. 4: 370-7 (1974).

Capaccioli et al., Cationic lipids improve antisense oligonucleotide uptake and prevent degradation in cultured cells and inhuman serum, Biochem. Biophys. Res. Commun., 197(2): 818-25 (1993).

Caravan et al., The interaction of MS-325 with human serum albumin and its effect on proton relaxation rates, J. Am. Chem. Soc., 124(12):3152-62 (2002).

(56) References Cited

OTHER PUBLICATIONS

Caravan, Strategies for increasing the sensitivity of gadolinium based MRI contrast agents, Chem. Soc. Rev., 35(6):512-23 (2006).
Castoldi et al., A sensitive array for microRNA expression profiling (miChip) based on locked nucleic acids (LNA), RNA. 12: 913-20 (2006).
Charreyre et al., Fluorescence energy transfer study of the conformation of oligonucleotides covalently bound to polystyrene latex particles. Langmuir, 13: 3103-10 (1997).
Chavany et al., Polyalkylcyanoacrylate nanoparticles as polymeric carriers for antisense oligonucleotides, Pharma. Res., 9(4): 441-9 (1992).
Chavany, et al., Adsorption of oligonucleotides onto polyisohexylcyanoacrylate nanoparticles protects them against nucleases and increases their cellular uptake. Pharma. Res., 11(9): 1370-8 (1994).
Chen et al., Kinetics and thermodynamics of DNA hybridization on gold nanoparticles, Nucl. Acids Res., 37: 3756-65 (2009).
Cheung et al., Akt3 and mutant V600E B-Raf cooperate to promote early melanoma development, Cancer Res., 68:3429-39 (2008).
Chirila et al., The use of synthetic polymers for delivery of therapeutic antisense oligodeoxynucleotides. *Biomaterials*, 23: 321-42 (2002).
Chithrani et al., "Determining the size and shape dependence of gold nanoparticle uptake into mammalian cells," *Nano Lett.* 6: 662-8 (2006).
Chithrani et al., "Elucidating the mechanism of cellular uptake and removal of protein-coated gold nanoparticles of different sizes and shapes," *Nano Lett.* 7: 1542-50 (2007).
Chrisey et al., Covalent attachment of synthetic DNA to self-assembled monolayer films, Nucl. Acids Res., 24: 3031-9 (1996).
Cload et al., "Polyether tethered oligonucleotide probes," *J. Am. Chem. Soc.* 113: 6324-6 (1991).
Cook, *Anti-Cancer Drug Design*. 6: 585-607 (1991).
Crawford et al., A novel B-RAF inhibitor blocks interleukin-8 (IL-8) synthesis in human melanoma xenografts, revealing IL-8 as a potential pharmacodynamic biomarker, *Mol. Cancer Ther.*, 7:492-9 (2008).
Crawford et al., Peptide aptamers: Tools for biology and drug discovery. 2(1): 72-9 (2003).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. Ann. Rev. Med., 55: 61-95 (2004).
Curtis et al., "A morphology-selective copper organosol," *Angew. Chem. Int. Ed. Engl.* 27: 1530-3 (1988).
Daniel et al., "Gold nanoparticles: assembly, supramolecular chemistry, quantum-size-related properties, and applications otward biology, catalysis, and nanotechnology," *Chem. Rev.* 104: 293-246 (2004).
Dankort et al., A new mouse model to explore the initiation, progression, and therapy of BRAFV600E-induced lung tumors, Genes Dev., 21: 379-84 (2007).
Dankort et al., Braf(V600E) cooperates with Pten loss to induce metastatic melanoma, Nat Genet., 41: 544-52 (2009).
Davies et al., A novel AKT3 mutation in melanoma tumours and cell lines, Br. J. Cancer, 99: 1265-8 (2008).
De Mesmaeker et al., "Antisense Oligonucleotides," *Acc. Chem. Res.* 28: 366-374 (1995).
Debouttiere et al., "Design of gold nanoparticles for magnetic resonance imaging," Adv. Funct. Mater., 16:2330 (2006).
Demers et al., Combinatorial templates generated by dip-pen nanolithography for the formation of two-dimensional particle arrays, Angew. Chem. Int. Ed., 40: 3071-3 (2003).
Devlin et al., Random peptide libraries: a source of specific protein binding molecules, Science, 249: 404-6 (1990).
Dhar et al., Polyvalent oligonucleotide gold nanoparticle conjugates as delivery vehicles for platinum(IV) warheads. *J. Am. Chem. Soc.*, 131(41): 14652-3 (2009).

Dhar et al., Targeted single wall carbon nanotube mediated Pt(IV) prodrug delivery using folate as a homing device. *J. Am. Chem. Soc.*, 130(34): 11467-76 (2008).
Dhomen et al., BRAF signaling and targeted therapies in melanoma, Hematol. Oncol. Clin. North Am., 23: 529-45, ix (2009).
Donachie, The cell cycle of *Escherichia coli.*, *Annu. Rev. Microbiol.*, 47: 199-230 (1993).
Dreyfus et al., Simple quantitative model for the reversible associate of DNA coated colloids, Phys. Rev. Lett., 102: 048301 (2009).
Dubertret et al., Single-mismatch detection using gold-quenched fluorescent oligonucleotides, Nat. Biotechnol., 19: 365-70 (2001).
Duimstra et al., A gadolinium chelate for detection of beta-glucuronidase: a self-immolative approach, J. Am. Chem. Soc., 127(37):12847-55 (2005).
Dulkeith et al., Gold nanoparticles quench fluorescence by phase induced radiative rate suppression, Nano Lett., 5: 585-9 (2005).
Durand et al., "Circular dichroism studies of an oligodeoxyribonucleotide containing a hairpin lood made of a hexaethylene glycol chain: conformation and stability," Nucleic Acid Res. 18:6353-9 (1990).
Dykxhoorn et al., Killing the messenger: short RNAs that silence gene expression, Nat. Rev. Mol. Cell Biol., 4(6):457-67 (2003).
Eckstein (Ed.) Oligonucleotides and Analogues, 1st Ed. Oxford University Press, New York (1991).
Elaissari et al., Effect of charge nature on the adsorption of single-stranded DNA fragments onto latex particles. J. Colloid Interface Sci., 202: 251-60 (1998).
Elghanian et al., "Selective coloimetric detection of polynucleotides based on the distance-dependent optical properties of gold nanoparticles," *Science.* 277:1078-81 (1997).
Eltekova et al., "Adsorption of aromatic compounds from solutions on titanium dioxide and silica," Langmuir. 3:951-7 (1987).
Endres et al., DNA-Ti02 nanoconjugates labeled with magnetic resonance contract agents. *J. Am. Chem. Soc.* 129(51): 15760-1 (2007).
Englisch et al., "Chemically modified oligonucleotides as probes and inhibitors," *Angewandte Chemie, International Edition.* 30: 613-722 (1991).
Enustun et al., "Coagulation of colloidal gold," *J. Am. Chem. Soc.* 85: 3317-28 (1963).
Fahy et al., Design and synthesis of polyacrylamide-based oligo-nucleotide supports for use in nucleic acid diagnostics, Nucl. Acids Res., 21: 1819-26 (1993).
Fattal et al., "Biodegradable polyalkylcyanoacrylate nanoparticles for the delivery of oligonucleotides," J. Controlled Release. 53: 137-143 (1998).
Faulds et al., Evaluation of surface-enhanced resonance Raman scattering for quantitative DNA analysis. Anal. Chem., 76: 412-7 (2004).
Femino et al., Visualization of single RNA transcripts in situ. Science, 280: 585-90 (1998).
Ferentz et al., "Disulfide cross-linked oligonucleotides" J. Am. Chem. Soc. 113:4000-2 (1991).
Final Office Action issued in connection with U.S. Appl. No. 11/917,680, dated Nov. 10, 2010.
Final Office Action issued in connection with U.S. Appl. No. 11/917,680, dated Nov. 10, 2011.
Flandroy et al., (D, L)Polyactide microspheres as embolic agent. *Neuroradiology*, 32: 311-5 (1990).
Freier et al., "The ups and downs of nucleic acid duplex stability: structure-stability studies on chemically-modified DNA:RNA duplexes," Nucleic Acid Res. 25: 4429-43 (1997).
Frens, "Controlled nucleation for the regulation of the particle size in monodisperse gold suspensions," Nature Phys. Sci. 241:20-2 (1973).
Frullano et al., Multimodal MRI contrast agents, J. Biol. Inorg. Chem., 12(7):939-40 (2007).
Gao et al., Secondary structure effects on DNA hybridization kinetics: a solution versus surface comparison. Nucl. Acids Res., 34: 3370-7 (2006).
Gerdes et al., Experimental determination and system level analysis of essential genes in *Escherichia coli* MG1655. *J. Bacteriol.*, 185: 5673-84 (2003).

(56) References Cited

OTHER PUBLICATIONS

Gestwicki et al., Influencing receptor-ligand binding mechanisms with multivalent ligand architecture. J. Am. Chem. Soc., 124: 14922-33 (2002).
Gidwani et al., Hybridization kinetics of double-stranded DNA probes for rapid molecular analysis. Analyst, 134: 1675-81 (2009).
Giljohann et al., Gene regulation with polyvalent siRNA-nanoparticle conjugates. J. Am. Chem. Soc., 131:2072-3 (2009).
Giljohann, et al., "Oligonucleotide loading determines cellular uptake of DNA-modified gold nanoparticles," Nano Letters, 7(12):3818-3821 (2007).
Goel et al., Melanocytic nevus-like hyperplasia and melanoma in transgenic BRAFV600E mice. Oncogene, 28: 2289-98 (2009).
Grabar et al., "Preparation and characterization of Au colloid monolayers" Anal. Chem. 67: 735-43.
Guo et al., CELL-SELEX: Novel perspectives of aptamer-based therapeutics, Int. J. Mol. Sci., 9: 668-78 (2008).
Hale et al., Recruitment of ZipA to the septal ring of *Escherichia coli* is dependent on FtsZ and independent of FtsA. *J. Bacteriol.*, 181: 167-76 (1999).
Hamilton et al., A species of small antisense RNA in post-transcriptional gene silencing in plants. Science, 286: 950-2 (1999).
Hammond et al., An RNA-directed nuclease mediates post-transcriptional gene silencing in *Drosophilia* cells. Nature, 404: 293-6 (2000).
Han et al., A gold nanoparticle based approach for screening triplex DNA binders, J. Am. Chem. Soc., 128(15):4954-5 (2006).
Hayashi et al., "Ultrafine particles," Physics Today. 44-60 (1987).
Hayashi et al., "Ultrafine particles," Vac. Sci. Technol. Jul./Aug. A5: 1375-84 (1987).
Hayatt, Colloidal Gold—Principles, Methods and Applications, vol. 1, Table of Contents pp. v-xvii; vol. 2 Table of Contents pp. v-xix; vol. 3 Table of Contents pp. v-xiv (1989).
He et al., "Colloidal Au-Enhanced Surface Plasmon Resonance for Ultrasensitive Detection of DNA Hybridization," J. Am. Chem. Soc. 122:9071-7 (2000).
Henglein et al., "Absorption spectrum and some chemical reactions of colloidal platinum in aqueous solutions," J. Phys. Chem. 99:14129-36 (1995).
Henglein, "Mechanism of reactions on colloidal microelectrodes and size quantization effects," Top. Curr. Chem. 143: 113-80 (1988).
Henglein, Small-particle research: Physicochemistry properties of extremely small colloidal metal and semiconductor particles. Chem. Rev. 89: 1861-73 (1989).
Hickman et al., "Combining spontaneous molecular assembly with microfabrication to pattern surfaces: Selective binding of isonitriles to platinum microwires and characterization by electrochemistry and surface spectroscopy," J. Am. Chem. Soc. 111:7271-2 (1989).
Holen et al., Positional effects of short interfering RNAs targeting the human coagulation trigger tissue factor. Nucl. Acids Res., 30: 1757-66 (2002).
Hu et al., Advances in high-field magnetic resonance imaging, Annu. Rev. Biomed.Eng., 6:157-84 (2004).
Hubbard, "Electrochemistry of well-defined surfaces," Acc. Chem. Res. 13:177-84 (1980).
Hurst et al., Maximizing DNA loading on a range of gold nanoparticle sizes. Anal. Chem., 78: 8313 (2006).
Hussain, et al. "A novel anionic dendrimer for improved cellular delivery of antisense oligonucleotides," Journal of Controlled Release, 99:139-155 (2004).
Iler, The Chemistry of Silica, Chapter 6, Wiley & Sons: 622-729 (1979).
International Preliminary Report on Patentability for International Application No. PCT/US2006/022325, dated Dec. 17, 2007.
International Preliminary Report on Patentability for International Application No. PCT/US2008/053603, dated Aug. 11, 2009.
International Preliminary Report on Patentability for International Application No. PCT/US2008/065366, dated Dec. 1, 2009.
International Preliminary Report on Patentability for International application No. PCT/US2009/065822, dated May 24, 2011.
International Preliminary Report on Patentability for International Application No. PCT/US2010/020558, dated Jul. 12, 2011.
International Preliminary Report on Patentability for International Application No. PCT/US2010/044453, dated Feb. 7, 2012.
International Preliminary Report on Patentability for International Application No. PCT/US2010/044844, dated Feb. 7, 2012.
International Preliminary Report on Patentability, PCT/US2010/27363, dated Oct. 18, 2011.
International Preliminary Report on Patentability, PCT/US2010/47591, dated Mar. 6, 2012.
International Preliminary Report on Patentability, PCT/US2010/47594, dated Mar. 6, 2012.
International Search Report and Written Opinion for International Application No. PCT/US2006/022325, dated Oct. 20, 2006.
International Search Report and Written Opinion for International Application No. PCT/US2008/053603, dated Jul. 30, 2008.
International Search Report and Written Opinion for International application No. PCT/US2008/065822, dated Mar. 5, 2010.
International Search Report and Written Opinion for International Application No. PCT/US2010/020558, dated Mar. 9, 2010.
International Search Report and Written Opinion for International Application No. PCT/US2010/044453, dated Apr. 29, 2011.
International Search Report and Written Opinion for International Application No. PCT/US2010/044844, dated Apr. 27, 2011.
International Search Report and Written Opinion for International Application No. PCT/US2010/27363, dated Apr. 15, 2010.
International Search Report and Written Opinion for International Application No. PCT/US2010/47591, dated Oct. 4, 2010.
International Search Report and Written Opinion for International Application No. PCT/US2010/47594, dated Oct. 8, 2010.
Introducing Antisense Oligonucleotides into Cells, Innovation & Precision in Nucleic Acid Synthesis, Integrated DNA Technologies (2005).
Jackson et al., *Escherichia coli* O157:H7 diarrhoea associated with well water and infected cattle on an Ontario farm, *Epidemiol. Infect.*, 120:17-20 (1998).
Jason et al., "Toxicology of antisense therapeutics," Toxic. and Appl. Pharm. 201: 66-83 (2004).
Jen et al., "A nonviral transfection approach in vitro: the design of a gold nanoparticle vector joint with microelectromechanical systems," Langmuir. 20:1369-74 (2004).
Jeong, et al. "Novel Intracellular Delivery System of Antisense Oligonucleotide by Self-Assembled Hybrid Micelles Composed of DNA/PEG Conjugate and Cationic Fusogenic Peptide," Bioconjugate Chem, 14:473-479 (2003).
Jin et al., What controls the melting properties of DNA-linked gold nanoparticle assemblies? J. Am. Chem. Soc., 125: 1643 (2003).
Jschke et al., "Automated incorporation of polyethylene glycol into synthetic oligonucleotides," Tetrahedron Lett. 34:301-4 (1993).
Kalman et al., Potentiometric and relaxometric properties of a gadolinium-based MRI contrast agent for sensing tissue pH, Inorg. Chem., 46(13):5260-70 (2007).
Katz et al., Integrated nanoparticle-biomolecule hybrid systems: synthesis, properties, and applications, Angew. Chem. Int. Ed., 43: 6042-108 (2004).
Katz, The reversible reaction of sodium thymonucleate and mercuric chloride, *J. Am. Chem. Soc.*, 74: 2238-45 (1952).
Kim et al., Biodegradable quantum dot nanocomposites enable live cell labeling and imaging of cytoplasmic targets, Nano Lett., 8(11):3887-92 (2008).
Kloosterman et al., In situ detection of miRNAs in animal embryos using LNA-modified oligonucleotide probes, Nat. Methods, 3: 27-9 (2006).
Kolarova et al., Preparation of magnetic oligo (dT) particles, Biotechniques, 20: 196-8 (1996).
Kopylov et al., Combinatorial chemistry of nucleic acids: SELEX, Mol. Biol., 34: 940-54 (2000).
Kosturko et al., The crystal and molecular structure of a 2:1 complex of 1-methylthymine-mercury(II), Biochem., 13: 3949-52 (1974).
Kroschwitz (Ed.) Concise Encyclopedia of Polymer Science and Engineering. John Wiley & Sons. 858-9 (1990).

(56) References Cited

OTHER PUBLICATIONS

Kukowski-Latallo et al., "Efficient transfer of genetic material into mammalian cells using starburst polyamidoamine dendrimers," Proc. Natl. Acad. Sci. USA. 93: 4897-902 (1996).
Lannutti et al., Human angiostatin inhibits murine hemangioendothelioma tumor growth in vivo, Cancer Res., 57: 5277-80 (1997).
Lebedeva et al., "Antisense oligonucleotides: promise and reality," Annu. Rev. Pharmacol. Toxicol. 41:403-19 (2001).
Lee et al., "Adsorption of ordered zirconium phosphonate multilayer films on silicon and gold surfaces," J. Phys. Chem. 92: 2597-2601 (1988).
Lee et al., Colorimetric detection of mercuric ion (Hg2+) in aqueous media using DNA-functionalized gold nanoparticles, Angew. Chem. Int. Ed. Engl., 46(22):4093-6 (2007).
Lemaigre et al., Transcriptional control of genes that regulate glycolysis and gluconeogenesis in adult liver, *Biochem. J.*, 303: 1-14 (1994).
Leunissen et al., Switchable self-protected attractions in DNA-functionalized colloids. Nat. Mater., 8: 590-95 (2009).
Li et al., "A calcium-sensitive magnetic resonance imaging contrast agent," J. Am. Chem. Soc., 121:1413 (1999).
Lin et al., Effector/memory but not naive regulatory T cells are responsible for the loss of concomitant tumor immunity. J. Immunol., 182: 6095-104 (2009).
Lin et al., Modeling genomic diversity and tumor dependency in malignant melanoma. Cancer Res., 68: 664-73 (2003).
Lipshutz et al., High density synthetic oligonucleotide arrays. Nanotechnology, 14: R15-27 (2003).
Liu et al., Accelerated color change of gold nanoparticles assembled by DNAzymes for simple and fast colorimetric Pb2+ detection. J. Am. Chem. Soc., 126: 12298-305 (2004).
Liu et al., "Synthesis, stability, and cellular internalization of gold nanoparticles containing mixed peptide-poly(ethylene glycol) monolayers," Analytical Chemistry. 79: 2221-9 (2007).
Liu et al., ARDB—Antibiotic Resistance Genes Database. *Nucl. Acids Res.*, 37: D443-7 (2009).
Liu et al., Argonaute2 is the catalytic engine of mammalian RNAi. Science, 305(5689): 1437-41 (2004).
Liu et al., De-N-acetyl GM3 promotes melanoma cell migration and invasion through urokinase plasminogen activator receptor signaling-dependent MMP-2 activation. Cancer Res., 69: 8662-9 (2009).
Liu et al., "New poly(D-glucaramidoamine)s induce DNA nanoparticle formation and efficient gene delivery into mammalian cells," J. Am. Chem. Soc. 126: 7422-3 (2004).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Loeken, Effects of mutation of the CREB binding site of the somatostatin promoter on cyclic AMP responsiveness in CV-1 cells. *Gene Expr.*, 3: 253-64 (1993).
Love et al., Self-assembled monolayers of thiolates on metals as a form of nanotechnology. Chem. Rev., 105: 1103-69 (2005).
Lutkenhaus et al., Bacterial cell division and the Z ring. *Annu. Rev. Biochem.*, 66: 93-116 (1997).
Lytton-Jean et al., "A thermodynamic investigation into the binding properties of DNA functionalized gold nanoparticle probes and molecular fluorophore probes," J. Am. Chem. Soc. 12:12754-5 (2005).
Ma et al., "Design and synthesis of RNA miniduplexes via a synthetic linker approach," Biochemistry. 32:1751-8 (1993).
Ma et al., "Design and synthesis of RNA miniduplexes via a synthetic linker approach. 2. Generation of covalently closed, double-stranded cyclic HIV-1 TAR RNA analogs with high Tat-binding affinity," Nucleic Acid Res. 21: 2585-9 (1993).
Major et al., Bioresponsive, cell-penetrating, and multimeric MR contrast agents, Acc. Chem. Res., 42(7):893-903 (2009).
Major et al., The synthesis and in vitro testing of a zinc-activated MRI contrast agent, Proc. Natl. Acad. Sci. USA, 104(35):13881-6 (2007).

Maoz et al., "Penetraction-controlled reactions in organized monolayer assemblies. 2. Aqueous permanganate interaction with self-assembling monolayers of long-chain surfactants," Langmuir. 3:1045-51 (1987).
Maoz et al., "Penetration-controlled reactions in organized monolayer assemblies. 1. Aqueous permanganate interaction with monolayer and multilayer films of long-chain surfactants," Langmuir. 4:1034-44 (1987).
Marinakos et al., "Gold nanoparticles as templates for the synthesis of hollow nanometer-sized conductive polymer capsules," Adv. Mater. 11: 34-7 (1999).
Marinakos et al., Template Synthesis of One-Dimensional Au, Au-Poly(pyrrole), and Poly(pyrrole) Nanoparticle Arrays, Chem. Mater. 10: 1214-19 (1998).
Martin et al., "Ein neuer Zugang zu 2-O-Alkylribonucleosiden and Eigenschaften deren Oligonucleotide," Helv. Chim. Acta. 78: 486-504 (1995) [Abstract only].
Martinez et al., Locked nucleic acid based beacons for surface interaction studies and biosensor development. Anal. Chem., 81: 3448-54 (2009).
Maruyama, et al., Nanoparticle DNA carrier with poly(L-lysine) grafted polysaccharide copolymer and poly(D,L-lactic acid). Bioconjugate Chem., 8: 735-742 (1997).
Massart, "Preparation of aqueous magnetic liquids in alkaline and acidic media," IEEE Transactions on Magnetics. 17:1247-8 (1981).
Matsuura et al., Construction and characterization of protein libraries composed of secondary structure modules. Protein Sci., 11: 2631-43 (2002).
Matteucci et al., "Synthesis of deoxyoligonucleotides on a polymer support," *J. Am. Chem. Soc.* 103: 3185-91 (1981).
Mattson et al., A practical approach to crosslinking. *Molec. Biol. Rep.*, 17: 167-83 (1993).
Maxwell et al., "Self-assembled nanoparticle probes for recognition and detection of biomolecules," *J. Am. Chem. Soc.* 124:9606-12 (2002).
Maye et al., A simple method for kinetic control of DNA-induced nanoparticle assembly. J. Am. Chem. Soc., 128: 14020-1 (2006).
Mayer (ed.), Nucleic Acid and Peptide Aptamers: Methods and Protocols (Humana Press, 2009).
McCurdy et al., "Deoxyligonucleotides with inverted polarity: synthesis and use in triple-helix formation," Nucleosides & Nucleotides. 10:287-90 (1991).
McGehee et al., Differentiation-specific element: a cis-acting developmental switch required for the sustained transcriptional expression of the angiotensinogen gene during hormonal-induced differentiation of 3T3-L1 fibroblasts to adipocytes. Mol. Endocrinol., 7: 551-60 (1993).
McKenzie et al., Sequence-specific DNA detection using high-affinity LNA-functionalized gold nanoparticles. Small, 3(11): 1866-8 (2007).
Mendell, MicroRNAs: critical regulators of development, cellular physiology and malignancy, Cell Cycle, 4(9):1179-84 (2005).
Mesmaeker et al., "Backbone modifications in oligonucleotides and peptide nucleic acid systems," Current Opinion in Structural Biology. 5: 343-55 (1995).
Milne et al., An approach to gene-specific transcription inhibition using oligonucleotides complementary to the template strand of the open complex. *Proc. Natl. Acad. Sci. USA*, 97(7): 3136-41 (2000).
Mirkin et al., "A DNA-based method for rationally assembling nanoparticles into macroscopic materials," *Nature*. 382:607 (1996).
Mittal, Improving the efficiency of RNA interference in mammals, Nat. Rev. Genet., 5(5):355-65 (2004).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31)10828-9 (2009).
Matijevic (Ed.), MRS Bulletin, Publication of the Materials Research Society, 15(1): 16-47 (Jan. 1990).

(56) References Cited

OTHER PUBLICATIONS

Mucic et al., "Synthesis and characterization of DNA with ferrocenyl groups attached to their 5'-termini: electrochemical characterization of a redox-active nucleotide monolayer," Chem. Commun. 555-7 (1996).
Myers et al., "A cyclopentane conformational restraint for a peptide nucleic acid: design, asymmetric synthesis, and improved binding affinity to DNA and RNA," Org. Lett. 5:2695-8 (2003).
Nam et al., "Nanoparticle-based bio-bar codees for the ultrasensitive detection of proteins," Science. 301:1884-6 (2003).
Neilson et al., "Sequence selective recognition of DNA by strand displacement with thymine-substituted polyamide," Science. 254:1497-1500 (1991).
Nitin et al., Peptide-linked molecular beacons for efficient delivery and rapid mRNA detection in living cells. Nucl. Acids Res., 32: e58 (2004).
Non-Final Office Action issued in connection with U.S. Appl. No. 11/917,680, dated Jun. 8, 2011.
Non-Final Office Action issued in connection with U.S. Appl. No. 12/526,560, dated Mar. 15, 2012.
Non-Final Office Action issued in connection with U.S. Appl. No. 12/625,537, dated May 23, 2012.
Non-Final Office Action issued in connection with U.S. Appl. No. 12/684,836, dated Jan. 6, 2012.
Non-Final Office Action issued in connection with U.S. Appl. No. 12/684,836, dated May 17, 2012.
Non-Final Office Action issued in connection with U.S. Appl. No. 12/724,395, dated Feb. 17, 2012.
Notice of Allowance issued in connection with U.S. Appl. No. 11/917,680, dated Apr. 26, 2012.
Nuzzo et al., "Spontaneous organized molecular assemblies. 3. Preparation and properties of solution adsorbed monolayers of Organic Disulfides on Gold Surfaces," J. Am. Chem. Soc. 109:2358-68 (1987).
Nykypanchuk et al., DNA-guided crystallization of colloidal nanoparticles. Nature, 451: 549-52 (2008).
O'Meara et al., Capture of single-stranded DNA assisted by oligonucleotide modules. Anal. Biochem., 255: 195-203 (1998).
O'Reilly et al., Identification of an activating transcription factor (ATF) binding site in the human transforming growth factor-beta 2 promoter. J. Biol. Chem., 267: 19938-43 (1992).
Office action from U.S. Appl. No. 11/917,680 dated Nov. 10, 2011.
Ohuchi et al., In vitro method for the generation of protein libraries using PCR amplification of a single DNA molecule and coupled transcription/translation, Nucl. Acids Res., 26: 4339-46 (1998).
Olshavsky et al., "Organometallic synthesis of FaAs crystallites exhibiting quantum confinement," J. Am. Chem. Soc. 112:9438-9 (1990).
Ono et al., "DNA triplex formation of oligonucleotide analogues consisting of linker groups and octamer segments that have opposite sugar-phosphate backbone polarities," Biochemistry. 30:9914-21 (1991).
Opalinska et al., Nucleic-acid therapeutics: basic principles and recent applications. Nat. Rev. Drug Discov., 1: 503-14 (2002).
Parak et al., Biological applications of colloidal nanocrystals, Nanotechnol., 14: R15-27 (2003).
Park et al., Array-based electrical detection of DNA with nanoparticle probes. Science, 295: 1503-6 (2002).
Park et al., DNA-programmable nanoparticle cystrallization. Nature, 451: 553-6 (2008).
Park et al., Gold nanoparticles functionalised by Gd-complex of DTPA-bis(amide) conjugate of glutathione as an MRI contrast agent, Bioorg. Med. Chem. Lett., 18(23):6135-7 (2008).
Parrish et al., Functional anatomy of a dsRNA trigger: Differential requirement for the two trigger strands in RNA interference. Mol. Cell, 6: 1077-87 (2000).
Patel et al., Peptide antisense nanoparticles. Proc. Natl. Acad. Sci. USA, 105: 17222-6 (2008).
Patil et al., "DNA-based therapeutics and DNA delivery systems: a comprehensive review," AAPS Jour. 7:E61-77 (2005).
Paunecku et al., Godolinium-conjugated Ti02-DNA oligonucleotide nanocanjugates show prolonged intracellular retention period and T1-weighted contract enhancement in magnetic resonance images. Nanomedicine, 4(3): 201-7 (2008).
Peng et al., Real-time detection of gene expression in cancer cells using molecular beacon imaging: New strategies for cancer research. Cancer Res., 65: 1909-17 (2005).
Penn et al., Nanoparticles for bioanalysis. Curr. Opin. Chem. Biol., 7: 609-15 (2003).
Peracchi, Prospects for antiviral ribozymes and deoxyribozymes. Rev. Med. Virol., 14: 47-64 (2004).
Perlette et al., Real-time monitoring of intracellular mRNA hybridization inside single living cells. Anal. Chem., 73: 5544-50 (2001).
Pon, Solid-phase supports for oligonucleotide synthesis. Meth. Molec. Biol., 20: 465-96 (1993).
Prausnitz et al., Transdermal drug delivery, Nat. Biotechnol., 26: 1261-8 (2008).
Prigodich et al., Nano-flares for mRNA regulation and detection. ACS Nano, 3: 2147-52 (2009).
Prime et al., "Self-assembled organic monolayers: model systems for studying adsorption of proteins at surfaces," Science. 252:1164-7 (1991).
Raj et al., Stochastic mRNA synthesis in mammalian cells. PLoS Biol., 4(10): e309 (2006).
Rethore et al., Preparation of chitosan/polyglutamic acid spheres based on the use of polystyrene template as nonviral gene carrier. Tissue Engineering, 15(4): 605-13 (2009).
Riccelli et al., Hybridization of single-stranded DNA targets to immobilized complementary DNA probes: comparison of hairpin versus linear capture probes. Nucl. Acids Res., 29: 996-1004 (2001).
Richardson et al., "Tethered oligonucleotide probes. A strategy for the recognition of structured RNA," J. Am. Chem. Soc. 112:5109-11 (1991).
Rosi et al., Nanostructures in biodiagnostics. Chem Rev., 105(4): 1547-62 (2005).
Rosi, et al., "Oligonucleotide-modified gold nanoparticles for intracellular gene regulation," Science 312(5776):1027-1030 (2006).
Sambrook, Molecular Cloning—A Laboratory Manual, 2nd Edition, Table of Contents pp. v-xxxii (1989).
Sandhu, et al. "Gold Nanoparticle-Mediated Transfection of Mammalian Cells," Bioconjugate Chem. 13:3-6 (2002).
Sanghvi., Chapter 15: Antisense Research and Application, CRC Press (1993).
Santangelo et al., Dual FRET molecular beacons for mRNA detection in living cells. Nucl. Acids Res., 32:e57 (2004).
Santangelo et al., Nanostructured probes for RNA detection in living cells. Ann. Biomed. Eng., 34:39-50 (2006).
Schifferlers et al., Cancer siRNA therapy by tumor selective delivery with ligand-targeted sterically stabilized nanoparticle. Nucl. Acid Res., 32(19): e149 (2004).
Schmid (Ed.) Clusters and Colloids, VCH, Weinheim (1994).
Seela et al., "Oligodeoxyribonucleotides containing 1,3-propanediol as nucleoside substitute," Nucleic Acid Res. 15: 3113-29 (1987).
Seelig et al., Catalyzed relaxation of a metastable DNA fuel. J. Am. Chem. Soc., 128: 12211-20 (2006).
Seferos et al., Locked nucleic acid-nanoparticle conjugates. Chembiochem., 8: 1230-2 (2007).
Seferos et al., Nano-flares: probes for transfection and mRNA detection in living cells. J. Am. Chem. Soc., 129: 15477-9 (2007).
Seferos et al., Polyvalent DNA nanoparticle conjugates stabilize nucleic acids. Nano Lett., 9: 308-11 (2009).
Sharma et al., Mutant V599EB-Raf regulates growth and vascular development of malignant melanoma tumors. Cancer Res., 65: 2412-21 (2005).
Sharma et al., Targeting Akt3 signaling in malignant melanoma using isoselenocyanates. Clin. Cancer Res., 15:.1674-85 (2009).
Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).
Sharp et al., RNA interference—2001. Genes Dev., 15: 485-90 (2001).

(56) References Cited

OTHER PUBLICATIONS

Simmel et al., DNA nanodevices. Small, 1: 284-99 (2005).
Smith et al., Bioconjugated quantum dots for in vivo molecular and cellular imaging, Adv. Drug Deliv. Rev., 60(11):1226-40 (2008).
Sokol et al., Real time detection of DNA.RNA hybridization in living cells. Proc. Natl. Acad. Sci. USA, 95: 11538-43 (1998).
Song et al., Synthesis of multimeric MR contrast agents for cellular imaging, J. Am. Chem. Soc., 130(21):6662-3 (2008).
Soriaga et al., "Determination of the orientation of aromatic molecules adsorbed on platinum electrodes. The effect of solute concentration," J. Am. Chem. Soc. 104:3937-45 (1982).
Srivastava et al., Use of riboprobes for northern blotting analysis. Biotechniques, 11(5): Abstract (1991).
Stahl et al., Deregulated Akt3 activity promotes development of malignant melanoma, Cancer Res., 64: 7002-10 (2004).
Stephenson et al., "Inhibition of Rous sarcoma viral RNA translation by a specific oligodeoxyribonucleotide," *Proc. Natl. Acad. Sci. USA.* 75:285-8 (1978).
Stoermer et al., Distance-dependent emission from dye-labeled oligonucleotides on striped Au/Ag nanowires: effect of secondary structure and hybridization efficiency. J. Am. Chem. Soc., 128: 13243-54 (2006).
Stoeva et al., Multiplexed detection of protein cancer markers with biobarcoded nanoparticle probes. J. Am. Chem. Soc., 128: 8378-9 (2006).
Storhoff et al., What controls the optical properties of DNA-linked gold nanoparticle assemblies? J. Am. Chem. Soc., 122: 4640-50 (2000).
Ow Sullivan et al., "Development of a novel gene delivery scaffold utilizing colloidal gold-polyethylenimine conjugates for DNA condensation," Gene Therapy 10:1882-90 (2003).
Sun et al., Ganglioside loss promotes survival primarily by activating integrin-linked kinase/Akt without phosphoinositide 3-OH kinase signaling. J. Invest. Dermatol., 119: 107-17 (2002).
Sundaram et al., "Particle-mediated delivery of recombinant expression vectors to rabbit skin induces high-titered polyclonal anisera (and circumvents purification of a protein immunogen)," *Nucl. Acid Res.* 24:1375-7 (1999).
Taton et al., Scanometric DNA array detection with nanoparticle probes, Science, 289(5485):1757-60 (2000).
Third party observations filed in European Application No. 08756546.1 dated Apr. 25, 2012.
Third party observations filed in European Application No. 08756546.1 dated Oct. 29, 2012.
Thomas et al., "Conjugation to gold nanoparticles enhances polyethylenimine's transfer of plasmid DNA into mammalian cells," Proc. Natl. Acad. Sci. USA. 100:9138-43 (2003).
Thomas et al., The interaction of HgCl2 with sodium thymonucleate. *J. Am. Chem. Soc.*, 76: 6032-4 (1954).
Thompkins et al., The study of the gas-solid interaction of acetic acid with a cuprous oxide surface using reflection-absorption spectroscopy. J. Colloid Interface Sci., 49: 410-21 (1974).
Thurn et al., Labeling TiO2 nanoparticles with dyes for optical fluorescence microscopy and determination of TiO2-DNA nanoconjugate stability. *Small*, 5(11): 1318-25 (2009).
Timmons et al., "Investigation of fatty acid monolayers on metal by contact," *J. Phys. Chem.* 69:984-90 (1965).
Tkachenko et al., "Multifunctional gold nanoparticle-peptide complexes for nuclear targeting," Am. Chem. Soc. 125: 4700-1 (2003).
Tkachenko et al., "Cellular trajectories of peptide-modified gold particle complexes: comparison of nuclear localization signals and peptide transduction domains," Bioconjugate Chem. 15: 482-90 (2004).
Tondelli et al., "Highly efficient cellular uptake of c-myb antisense oligonucleotides through specifically designed polymeric nanospheres," Nucl. Acid Res. 26: 5425-31 (1998).
Treisman, The SRE: a growth factor responsive transcriptional regulator. *Semin. Cancer Biol.*, 1:47-58 (1990).

Tsao et al., Genetic interaction between NRAS and BRAF mutations and PTEN/MMAC1 inactivation in melanoma. J. Invest. Dermatol., 122: 337-41 (2004).
Tuerk et al., Systematic evolution of ligands by exponential enrichment: RNA ligands to bacteriophage T4 DNA polymerase. Science, 249: 505-10 (1990).
Turberfield et al., DNA fuel for free-running nanomachines. Phys. Rev. Lett., 90: 118102 (2003).
Tyagi et al., Molecular beacons: Probes that fluoresce upon hybridization. Nat. Biotechnol., 14:303-8 (1996).
Ushida et al., "Gallium arsenide nanocrystals prepared in quinoline," J. Phys. Chem. 95:5382-4 (1992).
Vasiliskov et al., Parallel multiplex thermodynamic analysis of coaxial base stacking in DNA duplexes by oligodeoxyribonucleotide microchips. Nucl. Acids Res., 29: 2303-13 (2001).
Virmani et al., Comparison of two different methods for inoculating VX2 tumors in rabbit livers and hind limbs, J. Vasc. Interv. Radiol., 19(6):931-6 (2008).
Wang et al., Ganglioside GM3 inhibits matrix metalloproteinase-9 activation and disrupts its association with integrin, J. Biol. Chem., 278: 25591-9 (2003).
Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).
Wang et al., Inhibition of integrin-linked kinase/protein kinase B/Akt signaling: mechanism for ganglioside-induced apoptosis. J. Biol. Chem., 276: 44504-11 (2001).
Wang et al., "Nanometer-sized semiconductor clusters: materials synthesis, quantum size effects, and photophysical properties," J. Phys. Chem. 95:525-32 (1991).
Wang et al., Locked nucleic acid molecular beacons. J. Am. Chem. Soc., 127: 15664-5 (2005).
Wang et al., Molecular engineering of DNA: molecular beacons. Angew. Chem., Int. Ed., 48: 856-70 (2009).
Wang et al., Nanoparticles for multiplex diagnostics and imaging. Nanomedicine (Lond.), 1: 413-26 (2006).
Wang et al., Speeding up a single-molecule DNA device with a simple catalyst. Phys. Rev. E Stat. Nonlin. Soft Matter. Phys., 72: 051918 (2005).
Wang et al., Superparamagnetic sub-5 nm Fe@C nanoparticles: isolation, structure, magnetic properties, and directed assembly, Nano Lett., 8(11):3761-5 (2008).
Wasserman et al., "Structure and reactivity of alkylsiloxane monolayers formed by reaction of alkyltrichlorosilanes on silicon substrates," Langmuir. 5:1074-87 (1989).
Watson et al. (Eds.), *Molecular Biology of the Gene*, 4th ed., The Benjamin/Cummings Publishing Company Inc. (1987).
Wei et al., A study of the relationships between oligonucleotide properties and hybridization signal intensities from NimbleGen microarray datasets. Nucl. Acids Res., 36: 2926-38 (2008).
Wellbrock et al., V599EB-RAF is an oncogene in melanocytes. Cancer Res., 64: 2338-42 (2004).
Weller et al., "Colloidial semiconductor D-particles: Chemistry in the tradition region between solid state and molecules," Angew. Chem. Int. Ed. Engl. 32:41-53 (1993).
Whitesides, Proceedings of Robert A. Welch Foundation 39th Conference on Chemical Research Nanophase Chemistry. Houston, TX: 109-21 (1995).
Wolf et al., Rapid hybridization kinetics of DNA attached to submicron latex particles. Nucl. Acids Res., 15: 2911-26 (1987).
Xia, Nanomaterials at work in biomedical research, Nat. Mater., 7(10):758-60 (2008).
Xu et al., A gold-nanoparticle-based real-time colorimetric screening method for endonuclease activity and inhibition, Angew. Chem. Int. Ed. Engl., 46(19):3468-70 (2007).
Xu et al., Homogeneous detection of nucleic acids based upon the light scattering properties of silver-coated nanoparticle probes, Anal. Chem., 79(17):6650-4 (2007).
Xu et al., Thermodynamics of DNA hybridization on gold nanoparticles. J. Am. Chem. Soc., 127(38): 13227-31 (2005).
Yamane et al., On the complexing of desoxyribonucleic acid (DNA) by mercuric ion. *J. Am. Chem. Soc.*, 83: 2599-607 (1961).

(56) References Cited

OTHER PUBLICATIONS

Yan et al., Aptamers and aptamer targeted delivery. RNA Biol., 6: 316-20 (2009).
Yang et al., Evidence that processed small dsRNAs may mediate sequence-specific mRNA degradation during RNAi in *Drosophila* embryos. Curr. Biol., 10: 1191-200 (2000).
Ye et al., Characterization of a silencer regulatory element in the human interferon-gamma promoter. *J. Biol. Chem.*, 269: 25728-34 (1994).
You et al., Detection and identification of proteins using nanoparticle-fluorescent polymer 'chemical nose' sensors. Nat. Nanotechnol., 2: 318-23 (2007).
You et al., Engineering the nanoparticle-biomacromolecule interface. Soft Matter, 2: 190-204 (2006).
Zabner et al., Cellular and molecular barriers to gene transfer by a cationic lipid. J. Biol. Chem., 270: 18997-9007 (1995).
Zamecnik et al., "Inhibition of Rous sarcoma virus replication and cell transformation by a specific oligodeoxynucleotide," *Proc. Natl. Acad. Sci. USA*. 75:280-4 (1978).
Zamore et al., RNAi: double-stranded RNA directs the ATP-dependent cleavage of mRNA at 21 to 23 nucleotide intervals. Cell, 101: 25-33 (2000).
Zhang et al., "An extremely stable and orthogonal DNA base pair with a simplifed three-carbon backbone," J. Am. Chem. Soc., 127:74-5 (2005).
Zhang et al., Control of DNA strand displacement kinetics using toehold exchange. J. Am. Chem. Soc., 131: 17303-14 (2009).
Zhang et al., "PowerBLAST: A new network BLAST application for interactive or automated sequence analysis and annotation," Genome Res. 7:649-56 (1997).
Zhang et al., Single-quantum-dot-based DNA sensor. Nat. Mater., 4: 826-31 (2005).
Zhang, et al. "Gold Nanoparticles Decorated with Oligo(ethylene glycol) Thiols: Protein Resistance and Collidal Stability," J. Phys. Chem. 111:12229-12237 (2007).
Zheng et al., Aptamer nano-flares for molecular detection in living cells. Nano Lett., 9: 3258-61 (2009).
Zheng, et al. "Nanoparticles Comprising a Mixed Monolayer for Specific Bindings with Biomolecules," J. Am. Chem. Soc. 126:12047-12054 (2004).
Zimmer, Antisense oligonucleotide delivery with polyhexylcyanoacrylate nanoparticles as carriers. Methods, 18: 286-95 (1999).
Zimmerman et al., A novel silver(I)-mediated DNA base pair. J. Am. Chem. Soc., 124: 13684-5 (2002).
Rihova, Advanced Drug Delivery Reviews 29(3):273-89 (1998).
http://www.spectrumlabs.com/dialysis/PoreSize.html, Published by Spectrum Laboratories online, no volume, journal, title, page numbers; 1 page.
Sapra, et al. "Ligand-targeted liposomal anticancer drugs," Progress in Lipid Research 42:439-462 (2003).
He, et al. "Discovery of siRNA Lipid Nanoparticles to Transfect Suspension Leukemia Cells and Provide In Vivo Delivery Capability," Molecular Therapy, 22(2):359-70 (2014).
http://www.nanotherics.com/faq2.htm, published by nanoTherics, Staffordshire, United Kingdom, download Apr. 10, 2014, no author provided, no journal, no volume, no number, 6 pages long.
Reddy, et al. "Folate-targeted cationic liposome-mediated gene transfer into disseminated peritoneal tumors," Gene Therapy 9:1542-50 (2002).
Yin Win et al., "Effects of particle size and surface coating on cellular uptake of polymeric Nanoparticles for oral delivery of anticancer drugs," Biomaterials 26:2713-2722 (2005).
McManus et al., "Gene silencing in mammals by small interfering RNAs," Nat. Rev. Genet. 3:737-47 (2002).
International Search Report from PCT/US2008/065366, to Applicant Northwestern University and Inventors Mirkin et al., dated Dec. 9, 2008.
European Examination Report from corresponding European Application No. 08729548.1, dated Jan. 19, 2010.
International Search Report and Written Opinion for International Application No. PCT/US2010/55018, dated Dec. 9, 2010.
International Preliminary Report on Patentability for International Application No. PCT/US2010/55018, dated May 1, 2012.
Wang, et al. "DNA Binding of an Ethidium Intercalator Attached to a Monolayer-Protected Gold Cluster," Anal. Chem. 74:4320-4327 (2002).

\* cited by examiner

NUCLEIC ACID FUNCTIONALIZED NANOPARTICLES FOR THERAPEUTIC APPLICATIONS

CROSS REFERENCE TO RELATED APPLICATIONS

This application is a continuation of U.S. application Ser. No. 12/130,643, filed May 30, 2008, now U.S. Pat. No. 9,506,056, which claims the benefit of U.S. Provisional Application No. 60/985,462, filed Nov. 5, 2007 and U.S. Provisional Application No. 60/940,886, filed May 30, 2007, and is a continuation-in-part of International Application No. PCT/US06/22325, filed Jun. 8, 2006, each of which is incorporated by reference herein in its entirety.

STATEMENT OF GOVERNMENT INTEREST

This invention was made with government support under Grant Nos. 1 U54 CA119341-01 and U54 CA119341-02 awarded by The National Cancer Institute (NCI)/Centers of Cancer Nanotechnology Excellence (CCNE) and Grant Nos. 5 DPI OD000285-02 and DPI OD000285, awarded by the National Institute of Health (NIH Pioneer Award). The government has certain rights in the invention.

BACKGROUND

Nucleic acid-based methods for controlling gene expression have significantly impacted research involving gene pathways and function (Patil, et al., AAPS Jour, 7, E61 (2005), McManus, et al., Nat. Rev. Genet. 3, 737 (2002), Le-bedeva, et al., Annu. Rev. Pharmacol. Toxicol. 41, 403 (2001)). In addition, antisense therapies are potentially powerful candidates for clinical treatments of various ailments, including cancer, HIV/AIDS, and other diseases (Patil, et al., supra., Jason, et al., Toxic. And Appl. Pharm. 201, 66 (2004)). One antisense agent, Vitravene™, is currently used to treat retinitis in AIDS patents (Patil, et al., supra.). In conventional antisense approaches, oligonucleotides designed to hybridize with target mRNA sequences are delivered to a cell in a variety of ways. This hybridization leads to a down-regulation in the expression of the corresponding translated proteins. While the potential of antisense oligodeoxyonucleotides (ASODNs) was recognized over twenty years ago (Stephenson, et al., Proc. Not. Acad. Sci. U.S.A. 75, 285 (1978) Zamecnik, et al., Proc. Nat. Acad. Sci. U.S.A. 75, 280 (1978)), their development into viable therapeutic systems has faced challenges with regard to stable transfection and entry into diverse cell types, toxicity, and low efficacy. To address these fundamental barriers, various transfection agents have been developed to shuttle nucleic acids into cells. These include cationic lipids and polymers, modified viruses, dendrimers, liposomes, and nanoparticles (Patil, et al., supra, Jason, et al., supra., Bharali et al., Proc. Nat. Acad. Sci. U.S.A. 102, 11539 (2005), Bielinska, et al., Bioconjugate Chem. 10, 843 (1999)). Along with developments in delivery platforms, efforts have focused on developing nucleic acid analogs and investigating their potential as ASODNs. These include ODNs having phosphorothioate- or morpholino-modified backbones and peptide nucleic acids (PNAs) (De Mesmaeker, et al., Acc. Chem. Res. 28, 366 (1995), Myers, et al., Org. Lett. 5, 2695 (2003)). In some cases, the modified ASODNs provide enhanced stability in the presence of cellular endo- and exonucleases and stronger binding affinity with complementary sequences. Most antisense experiments use modified ASODNs in combination with a delivery mechanism in order to achieve maximum efficacy. While many combinations of carriers and modified ASODNs show promise, no single system has emerged that is vastly superior to others. Typical methods such as using phosphorothioate ASODNs complexed with cationic lipid carriers are often only useful in serum-free transfectins and are semi-toxic to certain cell types, thus limiting their general utility and their potential in therapeutics.

Gold nanoparticles have proven to be extremely useful for diagnostic and other applications. Detailed studies of gold nanoparticles surface-functionalized with both nucleic acids and proteins demonstrate a number of unique and highly useful characteristics of such structures. For instance, oligonucleotides attached to gold nanoparticles bind more strongly and more specifically to complementary oligonucleotides than do oligonucleotides that are not attached to gold nanoparticles. These observations are, in general, associated with the surface density of the oligonucleotide on the nanoparticle (i.e., surface density). The change in hybridization of the oligonucleotide (bound to a nanoparticle) to a target polynuceltide is reflected in an increase in melting temperature ($T_m$), a sharper melting profile, and/or a decease in the dissociation constant ($K_{diss}$) of the resulting hybridization complex compare to hybridization of the free oligonucleotide and the target polynucleotide. These binding events can furthermore alter the physical, electronic and optical properties of the gold nanoparticles in useful ways such as producing characteristic spectral shifts upon the specific binding of an attached oligonucleotide to its complement. Carbohydrates, lipids and proteins such as antibodies can also be attached to gold nanoparticles either individually or in combination.

To improve upon current methods, there exists a need in the art for an ideal antisense system that would feature high uptake efficiencies across many cell types, high intracellular stability, and a strong binding affinity to target mRNA, while maintaining a very low toxicity to either non-targeted cells when the application requires cell killing, or toward the targeted cells when gene manipulation is desired for other applications.

SUMMARY OF THE INVENTION

In an embodiment of the invention, a method of modulating cellular uptake of a first functionalized nanoparticle compared to a second functionalized nanoparticle is provided comprising the step of modulating packing density of a binding agent functionalized on the first nanoparticle, wherein a higher packing density results in increased cellular uptake of the functionalized nanoparticle compared to the second nanoparticle functionalized at a lower packing density. In one aspect, the binding agent is a oligonucleotide and in another aspect, the binding agent is a polypeptide. In various aspects, the packing density of the oligonucleotide on the surface of the first nanoparticle is increased by at least 1 oligonucleotide per nanoparticle. In alternative aspects, the packing density of the oligonucleotide on the surface of the first nanoparticle is increased by at least 5 oligonucleotides per nanoparticle, by at least 10 oligonucleotides per nanoparticle, by at least 20 oligonucleotides per nanoparticle, by at least 40 oligonucleotides per nanoparticle, by at least 60 oligonucleotides per nanoparticle, or by at least 80 oligonucleotides per nanoparticle. In still other aspects, uptake of the first functionalized nanoparticle is increased by at least 50% compared to the second nanoparticle, or by at least 100% compared to the second nanoparticle.

Methods provided also include modulating effectiveness of a therapeutic agent comprising the step of administering said therapeutic agent concomitantly with an oligonucleotide-functionalized nanoparticle, wherein said oligonucleotide-functionalized nanoparticle comprises an oligonucleotide comprising a sequence that modulates the effectiveness of said therapeutic agent.

In various aspects of the methods, cellular localization of the therapeutic agent is controlled by the oligonucleotide-functionalized nanoparticle and in other aspects of the methods, the oligonucleotide sequence is a chemosensitizing antisense sequence. In certain aspects, the chemosensitizing antisense sequence increases the toxicity of the therapeutic agent.

Methods are also provided for modulating effectiveness of a therapeutic agent comprising the step of administering said therapeutic agent concomitantly with a oligonucleotide-functionalized nanoparticle, wherein concentration of the oligonucleotide-functionalized nanoparticle modulates the effectiveness of said therapeutic agent.

Additional methods are provided for specifically delivering a therapeutic agent comprising the step of administering said therapeutic agent concomitantly with a oligonucleotide-functionalized nanoparticle, wherein the oligonucleotide-functionalized nanoparticle comprises a targeting agent that specifically delivers said therapeutic agent.

In one embodiment, methods of inhibiting expression of a gene product are provided comprising the step of hybridizing a polynucleotide encoding the gene product with one or more oligonucleotides complementary to all or a portion of the polynucleotide, the oligonucleotide being bound to a nanoparticle, wherein hybridizing between the polynucleotide and the oligonucleotide occurs over a length of the polynucleotide with a degree of complementarity sufficient to inhibit expression of the gene product. In one embodiment, the oligonucleotide is covalently bound to the nanoparticle. In various aspects of the methods, the oligonucleotide bound to the nanoparticle and the polynucleotide exhibit at least one property selected from the group consisting of an increased melting temperature ($T_m$), a sharper melting profile, and an increased association (or decreased dissociation) binding constant for hybridization, compared to the oligonucleotide not bound to the nanoparticle and the polynucleotide. In another aspect, the oligonucleotide is bound to the nanoparticle at a surface density high enough to increase cooperative hybridization to the polynucleotide compared to the same oligonucleotide when not bound to said nanoparticle.

In various aspects, expression of the gene product is inhibited in vivo and expression of the gene product is inhibited in vitro. Methods are also provided wherein the oligonucleotide is bound to the nanoparticle through one or more sulfur linkages.

In various aspects of the methods, the oligonucleotide is bound to the nanoparticle through a 5' linkage and/or the oligonucleotide is bound to the nanoparticle through a 3' linkage. In another embodiment, one or more additional oligonucleotides are attached, indirectly, to a functionalized nanoparticle by hybridization of the additional oligonucleotide to an oligonucleotide functionalized on the nanoparticle surface. In yet another embodiment, one or more additional oligonucleotides are attached to an oligonucleotide, functionalized on the nanoparticle surface, through an internal linkage. Methods contemplate use of an oligonucleotide which comprises a tandem repeat of identical nucleotide sequences, and in various aspects, the tandem repeat comprises two identical nucleotide sequences, three identical nucleotide sequences, four identical nucleotide sequences, five identical nucleotide sequences, or five or more identical nucleotide sequences. In certain aspects, the identical nucleotide sequences in the tandem repeat are separated by a nucleotide spacer between each identical sequence.

Consistent with the embodiments described above, methods are also provided wherein two or more identical oligonucleotide sequences and at least one distinct oligonucleotide sequence are bound to the same nanoparticle, either individually bound to the nanoparticle or arranged in a tandem array as described above, with or without spacers as described herein.

In methods provided the target polynucleotide is a mRNA encoding the gene product and translation of the gene product is inhibited. Methods are also provided wherein the target polynucleotide is DNA in a gene encoding the gene product and transcription of the gene product is inhibited. In variations of this aspect, the DNA encodes the gene product or the DNA is complementary to a coding region for the gene product. Alternatively, the target DNA is a region or sequence which is necessary for DNA replication. Additional targets contemplated by the methods include without limitation microRNA (miRNA), small interfering RNA (siRNA), premiRNA, small hairpin RNA (shRNA), transfer RNA (tRNA), proteins, viruses and small molecules.

Methods are also provided wherein the target polynucleotide is a bacterial polynucleotide. In this embodiment, the bacterial polynucleotide is bacterial genomic DNA or RNA transcribed from bacterial genomic DNA.

Methods are also provided wherein the target polynucleotide is a viral polynucleotide. In this embodiment, the viral polynucleotide is viral genomic RNA, the viral polynucleotide is viral genomic DNA, or the viral polynucleotide is RNA transcribed from viral genomic DNA. In another embodiment, the viral polynucleotide is a segment of a viral genome that has been integrated into the genome of another organism.

In various aspect of the methods provided, expression of the gene product is inhibited by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% compared to expression in the absence of the oligonucleotide.

In still other aspects of the methods provided, the oligonucleotide is bound to the nanoparticle at a surface density of 0.3 pmol/cm$^2$, at least about 0.6 pmol/cm$^2$, at least about 0.9 pmol/cm$^2$, at least about 1.2 pmol/cm$^2$, at least about 1.5 pmol/cm$^2$, at least about 1.8 pmol/cm$^2$, at least about 2.1 pmol/cm$^2$, at least about 2.4 pmol/cm$^2$, at least about 2.7 pmol/cm$^2$, at least about 3.0 pmol/cm$^2$, at least about 3.3 pmol/cm$^2$, at least about 3.6 pmol/cm$^2$, at least about 3.9 pmol/cm$^2$, at least about 4.2 pmol/cm$^2$, at least about 4.5 pmol/cm$^2$, at least about 4.8 pmol/cm$^2$, at least about 5.1 pmol/cm$^2$, at least about 5.4 pmol/cm$^2$, at least about 5.7 pmol/cm$^2$, at least about 6.0 pmol/cm$^2$, at least about 6.3 pmol/cm$^2$, at least about 6.6 pmol/cm$^2$, at least about 6.9 pmol/cm$^2$, at least about 7.2 pmol/cm$^2$, at least about 7.5 pmol/cm$^2$, at least about 7.8 pmol/cm$^2$, at least about 8.1 pmol/cm$^2$, at least about 8.4 pmol/cm$^2$, at least about 8.7 pmol/cm$^2$, at least about 9.0 pmol/cm$^2$, at least about 9.3 pmol/cm$^2$, at least about 9.6 pmol/cm$^2$, at least about 9.9 pmol/cm$^2$, at least 10 pmol/cm$^2$, at least 15 pmol/cm$^2$, at least 20 pmol/cm$^2$, at least 10 pmol/cm$^2$, at least 25 pmol/cm$^2$, at least 30 pmol/cm$^2$, at least 35 pmol/cm$^2$, at least 40 pmol/cm$^2$, at least 45 pmol/cm$^2$, at least 50 pmol/cm$^2$, at least 55 pmol/cm$^2$, at least 60 pmol/cm$^2$, at least 65 pmol/cm$^2$, at least 70 pmol/cm$^2$, or at least 75 pmol/cm$^2$.

Methods include those wherein expression of the targeted gene product is associated with a disease state.

Methods also include those wherein the nanoparticle is optionally labeled.

Methods also include those wherein the nanoparticle further comprises a targeting molecule.

In various aspects of the methods, packing density of the oligonucleotides on the surface of the nanoparticle is sufficient to result in cooperative behavior between the nanoparticles.

In other aspects of the methods, packing density for the oligonucleotides on the surface of the nanoparticle is sufficient to enhance cellular uptake.

Methods are also provided wherein the target polynucleotide is an inhibitory RNA (including, without limitation, siRNA) that performs a regulatory function, the oligonucleotide is complementary to a regulatory region of the polynucleotide, the oligonucleotide is released from the nanoparticle after the nanoparticle enters a cell, and/or the nanoparticle includes a targeting moiety.

DETAILED DESCRIPTION OF THE INVENTION

Figure 1:
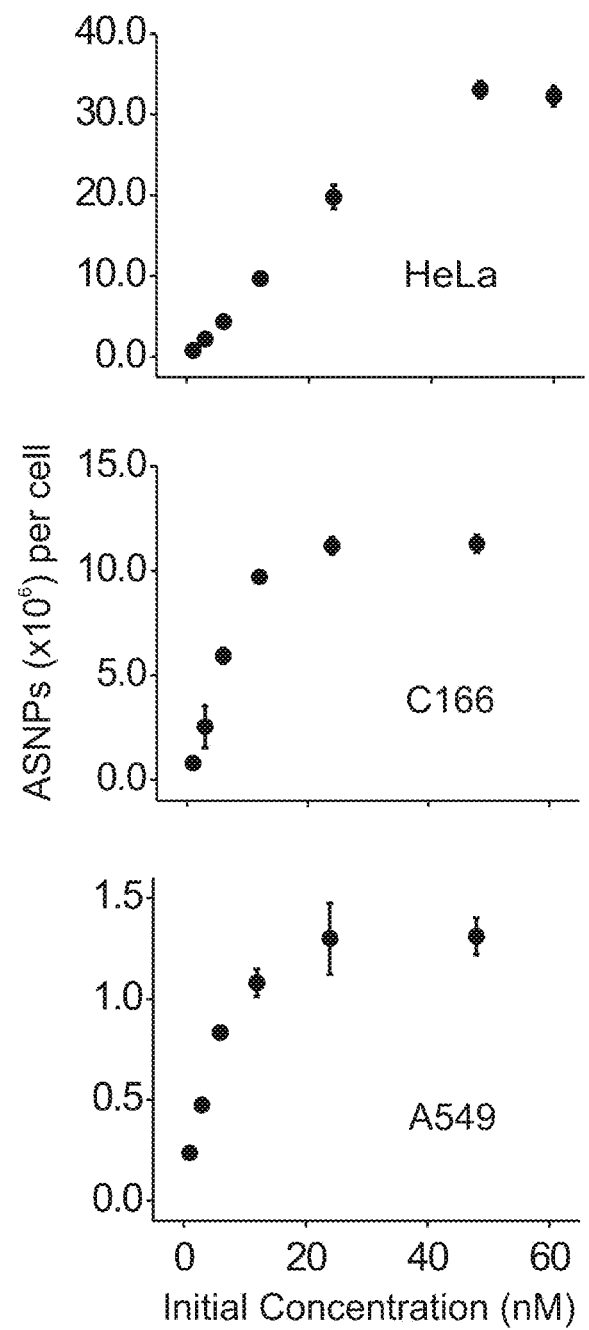
FIG. 1. Cellular uptake of ASNPs. Analysis of ASNPs in three different cell types (HeLa, C166, A549) shows that the number of ASNPs per cell is dependent on initial particle concentration and cell type.

Gold nanoparticles exhibit a variety of unique optical, electronic, and catalytic properties (Daniel, et al., Chem. Rev. 104, 293 (2004)), and owing to their affinity for biomolecules, they have been used extensively in immunostaining (Baudhuin, et al., Colloidal Gold: Principles, Methods, and Applications 2, 1 (1989)), as intracellular targeting agents (Tkachenko et al., Bioconjugate Chem. 15, 482 (2004)), and as non-viral vectors for DNA delivery (Thomas, et al., Proc. Nat. Acad. Sci. 100, 9138 (2003), Sundaram, et al., Nucl. Acids Res. 24, 1375 (1999), Sandhu, et al., Bioconjugate Chem. 13, 3 (2002), Sullivan, et al., Gene Therapy 10, 1882 (2003), Jen et al., Langmuir 20, 1369 (2004)). Developments in the last decade have shown that gold nanoparticles chemically functionalized with alkylthiol-terminated oligonucleotides (Mirkin, et al., Nature 382, 607 (1996)) are highly stable in saline solutions and bind complementary nucleic acids in a very selective and cooperative manner, resulting in equilibrium association constants that can be more than two orders of magnitude greater than those observed for unmodified oligonucleotides and their complements (Lytton-Jean, et al., J Am. Chem. Soc. 12?, 12754 (2005)). These unique properties have made oligonucleotide-functionalized gold nanoparticles the centerpiece of several highly sensitive and selective assays for biomolecule detection (Rosi, et al., Chem. Rev. 105, 1547 (2005), Elghanian, et al., Science 277, 1078 (1997), Nam, et al. Science 301, 1884 (2003), He et al., J Am. Chem. Soc. 122, 9071 (2000), Maxwell, et al., J Am. Chem. Soc. 124, 9606 (2002)). Due to their demonstrated stability and enhanced binding properties, it was hypothesized that these particles could potentially be used as efficient scavengers of intracellular DNA or RNA. Accordingly, methods are provided wherein oligonucleotide-functionalized gold nanoparticles are intrinsically new antisense agents that rely on the ensemble properties of the nanoparticle-oligonucleotide conjugate.

As is described in US Patent Application 20030147966 and elsewhere, it is also well known in the art that gold nanoparticles can pass through cell and, under suitable conditions, nuclear membranes, thus providing a means for labeling cells and for delivering materials into cells and cell nuclei. The utility of these previous methods is, however, limited by the relative instability of surface modified gold nanoparticles. These limitations have been partially addressed by means such as the inclusion of phosphorothioate linkages in the oligonucleotides attached to the nanoparticles in order to retard the degradation of the oligonucleotides by nucleases and by encapsulating the modified nanoparticles in proteinaceous and other protective sheaths.

As used herein, a "therapeutic agent" is any agent from which a therapeutic benefit is or can be derived from its administration or from which a therapeutic benefit would be expected from its administration regardless of whether the benefit is realized.

The utility of the methods provided is demonstrated by the use of the oligonucleotide-modified gold nanoparticles for the in vivo silencing of the expression of a cellular gene by suppressing the translation of the mRNA produced by that gene. In this application, the increase in the binding constant for gold nanoparticles to their complementary sequences by as much as 100× that results from the present invention is, in contrast to the prior art, such that the replication of the genomic sequence(s) bound to the gold-nanoparticle is completely prevented. This ability to silence gene expression can be used in the treatment of disease states that are characterized by the expression of proteins that are aberrant in structure or location. In certain aspects, the methods provided are used for the delivery of expressible genes, including double stranded polynucleotides, into cells in a manner that avoids the well known limitations of retroviral transduction and mechanical methods such as electroporation or "gene guns" that are employed for similar purposes. The utility of these methods can be further enhanced by modifying the gold nanoparticle such that both oligonucleotides and selective binding agents such as antibodies, lectins or cell-specific recognition elements such as RGD peptides or certain carbohydrates or glycoproteins are attached thereto so long as the oligonucleotide surface density is not reduced below the critical threshold level for stability. These cell-specific recognition elements permit the targeting of the oligonucleotide-modified gold nanoparticle to particular cells or cell types with the corresponding improvement in the efficacy of the treatment. In other aspects, the gold nanoparticles are surface functionalized with imaging contrast agents and, in various embodiments have magnetic cores that impart further advantages with respect to imaging and selective cellular targeting. When functionalized nanoparticles also include a label or imaging agent, entry into a target cell type can be quantitated by visualization or by direct or indirect detection. Quantitation of cell entry permits a precise determination of the number of nanoparticle entering a cell, which in turn allows for precise determination of appropriate dosages fro in vivo administration. In still other aspects, the gold nanoparticles are additionally functionalized with known small molecule therapeutic agents that augment the therapeutic efficacy of co-delivered species on the surface of the nanoparticles (e.g. DNA, proteins, carbohydrates, etc.).

In other aspects, methods are provided wherein the effects of a therapeutic agent are modulated comprising the step of administering the therapeutic agent concomitantly with an oligonucleotide-functionalized nanoparticle, wherein the oligonucleotide associates with the therapeutic agent through any mode of interaction thereby modulating the effectiveness of the therapeutic agent. In one aspect, methods are provided wherein the effects of a therapeutic agent are modulated comprising the step of administering said therapeutic agent and said oligonucleotide-functionalized nanoparticle sequentially, wherein either is administered first in the sequence. In another aspect, methods are provided wherein the effects of a therapeutic agent are modulated comprising the step of administering said therapeutic agent and said oligonucleotide-functionalized nanoparticle sequentially, wherein either the therapeutic agent or the oligonucleotide functionalized nanoparticle is administered, and after a period of time passes, this first administration is followed by administration of either the therapeutic agent or the oligonucleotide functionalized nanoparticle, whichever was not administered first. In various aspects, the period of time is at least about 1 minute, at least about 2 minutes, at least about 3 minutes, at least about 4, minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 1 hour, at least about 2 hours, at least about 3 hours, at least about 4 hours, at least about 5 hours, at least about 10 hours, at least about 15 hours, at least about 18 hours, at least about 24 hours, at least about 36 hours, at least about 2 days, at least about 3 days, at least about 4 days, at least about 5 days, at least about 6 days at least about 7 days, at least about 10 days, at least about 2 weeks, at least about 3 weeks, at least about 1 month, at least about 2 months, at least about 3 months, at least about 4 months, at least about 5 months, at least about 6 months or more.

In still other aspects, the effect of the therapeutic agent is modulated by administering a different amount of a functionalized nanoparticle relative to a previously administered amount to control the activity of a therapeutic agent. In some aspects, the amount is increased or decreased by at least 10%. In other aspects, the amount is increased or decreased by at least 20%, at least 30%, at least 40%, at least 50%, at least 60%, at least 70%, at least 80%, at least 90%, at least 2-fold, at least 4-fold, at least 6-fold, at least 8-fold, at least 10-fold, at least 20-fold, at least 50-fold, at least 100-fold or more.

In various aspects, the effect of the therapeutic agent is modulated by administering a different amount of a therapeutic agent relative to a previously administered amount to offset activity of a functionalized nanoparticle. In some aspects, the amount of the therapeutic agent that is administered is increased or decreased by at least 10%. In other aspects, the amount is increased or decreased by at least 20%, at least 30%, at least 40%, at least 50%, at least 60%, at least 70%, at least 80%, at least 90%, at least 2-fold, at least 4-fold, at least 6-fold, at least 8-fold, at least 10-fold, at least 20-fold, at least 50-fold, at least 100-fold or more.

In some aspects, the effectiveness of the therapeutic agent is altered by at least 10%, or at least 15%, or at least 20%, or at least 25%, or at least 30%, or at least 40%, or at least 50%, or at least 60%, or at least 70%, at least 80%, at least 90%, at least 95%, at least 2-fold, at least 5-fold, at least 10-fold, at least 20-fold, at least 50-fold or more compared to effectiveness of the therapeutic agent in the absence of the oligonucleotide-functionalized nanoparticle, regardless of the number of times either the therapeutic agent is administered and/or the number of times the oligonucleotide-functionalized nanoparticle is administered.

In various aspects, the effectiveness of the therapeutic agent is altered as a result of the oligonucleotide-functionalized nanoparticle causing localization of the therapeutic agent to the extent that effectiveness of the therapeutic agent is altered. In one aspect and without being bound to a mechanism, it is contemplated that binding or association of the therapeutic agent to or with an oligonucleotide-functionalized nanoparticle prevents the therapeutic agent from reaching its target area thereby decreasing effectiveness of the therapeutic agent. One of ordinary skill in the art will recognize that oligonucleotide-functionalized nanoparticles can be modified to localize the nanoparticle and thus in turn localize the therapeutic agent. Such modifications include, but are not limited to, intracellular localization and tissue-specific localization.

In another aspect, methods are provided wherein an antisense sequence functionalized on a nanoparticle is administered concomitantly or sequentially with a therapeutic agent whereby the antisense functionalized nanoparticle increases the effectiveness of the therapeutic agent. In this aspect and without being bound to a mechanism, the antisense sequence may bind not only to the therapeutic agent but also to a target mRNA of interest. In one aspect of this method, administration of the antisense functionalized nanoparticle enhances the effectiveness of the therapeutic agent, in another aspect administration of the antisense functionalized nanoparticle decrease the effectiveness of the therapeutic agent.

Accordingly, in various aspects of the invention methods are provided wherein an oligonucleotide-functionalized nanoparticle comprises a targeting agent directed to a non-target cell or tissue that decreases the effectiveness of a therapeutic agent specifically in said non-target cell or tissue by titrating said therapeutic agent specifically in said non-target cell or tissue.

In another aspect, a therapeutic agent is administered either concomitantly or sequentially with an antisense oligonucleotide-functionalized nanoparticle comprising a targeting agent direct to a target cell or tissue in combination with an oligonucleotide-functionalized nanoparticle comprising a targeting agent directed to a non-target cell or tissue, wherein the effectiveness of the therapeutic agent is increased in a target cell or tissue and decreased in a non-target cell or tissue. In aspects of the invention, antisense oligonucleotides may be selected that either increase or decrease the effectiveness of a therapeutic agent.

In other aspects, nanoparticles may be functionalized with polypeptides that can bind to a therapeutic agent to modulate said therapeutic agent's effectiveness. In some aspects, said polypeptide-functionalized nanoparticle may additionally contain a targeting agent. In another aspect, a method is provided wherein a therapeutic agent is administered either concomitantly or sequentially with two or more groups of functionalized nanoparticles wherein each group comprises a different targeting agent.

In still other aspects, methods are provided wherein multiple different therapeutic agents are used in combination with multiple nanoparticles functionalized with different oligonucleotides. In one aspect, the oligonucleotide-functionalized nanoparticles additionally include a targeting agent attached thereto.

Thus, methods of inhibiting expression of a gene product are provided comprising the step of hybridizing a polynucleotide encoding the gene product with one or more oligonucleotides complementary to all or a portion of the polynucleotide, the oligonucleotide being bound to a nanoparticle, wherein hybridizing between the polynucleotide and the oligonucleotide occurs over a length of the polynucleotide with a degree of complementarity sufficient to inhibit expression of the gene product. Methods wherein expression of the gene product is inhibited in vivo and/or in vitro are contemplated.

In another aspect, methods are provided to introduce a mutation in a polynucleotide of a cell comprising the step of contacting the cell with an oligonucleotide bound to a nanoparticle, wherein the oligonucleotide has a sequence that includes one or more bases that differ from the sequence of a target polynucleotide in the cell, and wherein the oligonucleotide is otherwise sufficiently complementary to the target polynucleotide to permit hybridization to the target polynucleotide, and further wherein hybridization allows for cross-over and/or recombination with the target polynucleotide during replication of the target polynucleotide. In one aspect, replication of the target polynucleotide occurs during cell division. In another aspect, replication of the target polynucleotide occurs during replication of the target polynucleotide which is extra-chromosomal. In various embodiments, the mutation which is introduced results in inhibited expression of a gene product encoded by the target polynucleotide, whether through modification of transcriptional and/or translational regulatory sequences in the target polynucleotide, or the mutation corrects one or more bases sequences in the target polynucleotide such that the gene product encoded by the target polynucleotide is expressed having the correct, or "naturally-occurring" amino acid sequence, and/or transcriptional and/or translational regulatory elements.

Nanoparticles

In general, nanoparticles contemplated include any compound or substance with a a high loading capacity for an oligonucleotide as described herein, including for example and without limitation, a metal, a semiconductor, and an insulator particle compositions, and a dendrimer (organic versus inorganic).

Thus, nanoparticles are contemplated which comprise a variety of inorganic materials including, but not limited to, metals, semi-conductor materials or ceramics as described in US patent application No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, $Fe^{+4}$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshavsky, et al., J. Am. Chem. Soc., 112, 9438 (1990); Ushida et al., J. Phys. Chem., 95, 5382 (1992).

In practice, methods of inhibiting gene expression are provided using any suitable particle having oligonucleotides attached thereto that are in general suitable for use in detection assays known in the art to the extent and do not interfere with complex formation, i.e., hybridization to a target polynucleotide. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preaparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Suitable nanoparticles are also commercially available from, for example, Ted Pella, Inc. (gold), Amersham Corporation (gold) and Nanoprobes, Inc. (gold).

Also as described in US patent application No 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent application No 20030147966, nanoparticles contemplated are produced using $HAuCl_4$ and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticle Size

In various aspects, methods provided include those utilizing nanoparticles which range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or amount surface area that can be derivatized as described herein.

Nanoparticle Targeting Agents

In certain embodiments of the methods, the nanoparticle is optionally labeled and in various aspects of these embodiment, the nanoparticle comprises one or more targeting moieties, including but not limited to proteins, including antibodies, peptides, small molecules, anticancer agents, polynucleotide-binding agents, carbohydrates, lipids, ligands for cell surface receptors, and the like. Targeting moieties are useful for delivery of the functionalized nanoparticle to specific cell types and/or organs, as well as sub-cellular locations.

Accordingly, targeting agent contemplated include nuclear localization signals (NLS) and peptide transduction domains, including, for example, SV40 large T NLS, HIV-1 TAT protein NLS, adenovirus NLS, integrin binding domain, oligolysince (each of which is described in (Tkachenko, et al., Bioconjugate Chem (2004) 15:482-490), and adenovirus fiber protein comprising both NLS and receptor-mediated endocytosis (RME) domains (Tkachenko, et al., Am. Chem. Soc. (2003) 125:4700-4701).

Oligonucleotide Features

Oligonucleotides contemplated for attachment to a nanoparticle include those which modulate expression of a gene product expressed from a target polynucleotide. Accordingly, antisense oligonucleotides which hybridize to a target polynucleotide and inhibit translation, siRNA oligonucleotides which hybridize to a target polynucleotide and initiate an RNAse activity (for example RNAse H), triple helix forming oligonucleotides which hybridize to double-stranded polynucleotides and inhibit transcription, and ribozymes which hybridize to a target polynucleotide and inhibit translation, are contemplated.

Each nanoparticle utilized in the methods provided has a plurality of oligonucleotides attached to it. As a result, each nanoparticle-oligonucleotide conjugate has the ability to bind to a plurality of target polynucleotides having a sufficiently complementary sequence. For example, if a specific mRNA is targeted, a single nanoparticle has the ability to bind to multiple copies of the same transcript. In one aspect, methods are provided wherein the nanoparticle is functionalized with identical oligonucleotides, i.e., each oligonucleotide has the same length and the same sequence. In other aspects, the nanoparticle is functionalized with two or more oligonucleotides which are not identical, i.e., at least one of the attached oligonucleotides differ from at least one other attached oligonucleotide in that it has a different length and/or a different sequence. In aspects wherein different oligonucleotides are attached to the nanoparticle, these different oligonucleotides bind to the same single target polynucleotide but at different locations, or bind to different target polynucleotides which encode different gene products Accordingly, in various aspects, a single functionalized nanoparticle may be used a method to inhibit expression of more than one gene product. Oligonucleotides are thus used to target specific polynucleotides, whether at one or more specific regions in the target polynucleotide, or over the entire length of the target polynucleotide as the need may be to effect a desired level of inhibition of gene expression.

Accordingly, the oligonucleotides are designed with knowledge of the target sequence. Methods of making oligonucleotides of a predetermined sequence are well-known. See, for example, Sambrook et al., Molecular Cloning: A Laboratory Manual (2nd ed. 1989) and F. Eckstein (ed.) Oligonucleotides and Analogues, Ist Ed. (Oxford University Press, New York, 1991). Solid-phase synthesis methods are contemplated for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Alternatively, oligonucleotides are selected from a library. Preparation of libraries of this type is well know in the art.

See, for example, Oligonucleotide libraries: United States Patent Application 20050214782, published Sep. 29, 2005.

In another aspect, methods are provided wherein the oligonucleotide is functionalized to the nanoparticle in such a way that the oligonucleotide is released from the nanoparticle after the nanoparticle enters a cell. In general an oligonucleotides can be release from the surface of a nanoparticle using either chemical methods, photon release (i.e., irradiating cells in which nanoparticles have entered using an electromagnetic wavelengths chosen based on the nanoparticle particle size), and changes in ionic or acid/base environment.

In one aspect of this embodiment, the oligonucleotide is attached to the nanoparticle via an acid-labile moiety and once the functionalized nanoparticle is taken into the cell via, for example, an endosome, acidification of the endosome (a normal part of endosomal uptake) releases the oligonucleotides. This aspect is particular useful in instances where the intent is to saturate the cell with for example, an siRNA and release from the nanoparticle would improve kinetics and resolve potential steric hindrance problems. RNAi for modulating gene expression is well known in the art and generally described in, for example, United States Patent Application 20060019917, United States Patent Application 20060008907 and United States Patent Application 20050059016, the disclosures of which are incorporated herein by reference in their entireties. Preparation of siRNA oligonucleotide libraries is generally described in United States Patent Application 20050197315 the disclosure of which is incorporated herein by reference in its entirety.

Oligonucleotide Length

The term "oligonucleotides" as used herein includes modified forms as discussed herein as well as those otherwise known in the art which are used to regulate gene expression. Likewise, the term "nucleotides" as used herein is interchangeable with modified forms as discussed herein and otherwise known in the art. In certain instances, the art uses the term "nucleobase" which embraces naturally-occurring nucleotides as well as modifications of nucleotides that can be polymerized into a molecule that functions as antisense. Herein, the terms "nucleotides" and "nucleobases" are used interchangeably to embrace the same scope unless otherwise noted.

Nanoparticles for use in the methods provided are functionalized with an oligonucleotide, or modified form thereof, which is from about 5 to about 100 nucleotides in length. Methods are also contemplated wherein the oligonucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated.

In still other aspects, oligonucleotides comprise from about 8 to about 80 nucleotides (i.e. from about 8 to about 80 linked nucleosides). One of ordinary skill in the art will appreciate that methods utilize compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotide in length.

Oligonucleotide Complementarity

"Hybridization" means an interaction between two strands of nucleic acids by hydrogen bonds in accordance with the rules of Watson-Crick DNA complementarity, Hoogstein binding, or other sequence-specific binding known in the art. Hybridization can be performed under different stringency conditions known in the art. Under appropriate stringency conditions, hybridization between the two complementary strands could reach about 60% or above, about 70% or above, about 80% or above, about 90% or above, about 95% or above, about 96% or above, about 97% or above, about 98% or above, or about 99% or above in the reactions. It will be understood by those of skill in the art that the degree of hybridization is less significant that a resulting degree of inhibition of gene product expression.

In various aspects, the methods include use of an oligonucleotide which is 100% complementary to the target polynucleotide, i.e., a perfect match, while in other aspects, the oligonucleotide is at least (meaning greater than or equal to) about 95% complementary to the polynucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the oligonucleotide to the extent that the oligonucleotide is able to achieve the desired degree of inhibition of a target gene product.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The percent complementarity is determined over the length of the oligonucleotide. For example, given an antisense compound in which 18 of 20 nucleotides of the antisense compound are complementary to a 20 nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In various aspect, the oligonucleotide has a sequence that introduces or induces changes in secondary structure of the target polynucleotide, including but not limited to one or more loops or hairpin structures.

Oligonucleotide Attachment

Oligonucleotides contemplated for use in the methods include those bound to the nanoparticle through any means. Regardless of the means by which the oligonucleotide is attached to the nanoparticle, attachment in various aspects is effected through a 5' linkage, a 3' linkage, some type of internal linkage, or any combination of these attachments.

In one aspect, the nanoparticles, the oligonucleotides or both are functionalized in order to attach the oligonucleotides to the nanoparticles. Methods to functionalize nanoparticles and oligonucleotides are known in the art. For instance, oligonucleotides functionalized with alkanethiols at their 3'-termini or 5'-termini readily attach to gold nanoparticles. See Whitesides, Proceedings of the Robert A. Welch Foundation 39th Conference On Chemical Research Nanophase Chemistry, Houston, Tex., pages 109-121 (1995). See also, Mucic et al. Chem. Commun. 555-557 (1996) which describes a method of attaching 3' thiol DNA to flat gold surfaces. The alkanethiol method can also be used to attach oligonucleotides to other metal, semiconductor and magnetic colloids and to the other types of nanoparticles described herein. Other functional groups for attaching oligonucleotides to solid surfaces include phosphorothioate groups (see, for example, U.S. Pat. No. 5,472,881 for the binding of oligonucleotide-phosphorothioates to gold surfaces), substituted alkylsiloxanes (see, for example, Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., Anal. Chem., 67, 735-743 for binding of aminoalkylsiloxanes and for similar binding of mercaptoaklylsiloxanes). Oligonucleotides with a 5' thionucleoside or a 3' thionucleoside may also be used for attaching oligonucleotides to solid surfaces. The following references describe other methods which may be employed to attached oligonucleotides to nanoparticles: Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langmuir, 3, 951 (1987) (aromatic carboxylic acids, aldehydes, alcohols and methoxy groups on titanium dioxide and silica); Lec et al., J. Phys. Chem., 92, 2597 (1988) (rigid phosphates on metals).

U.S. patent application Ser. Nos. 09/760,500 and 09/820,279 and international application nos. PCT/US01/01190 and PCT/US01/10071 describe oligonucleotides functionalized with a cyclic disulfide. The cyclic disulfides in certain aspects have 5 or 6 atoms in their rings, including the two sulfur atoms. Suitable cyclic disulfides are available commercially or are synthesized by known procedures. Functionalization with the reduced forms of the cyclic disulfides is also contemplated.

In certain aspects wherein cyclic disulfide functionalization, oligonucleotides are attached to a nanoparticle through one or more linkers. In one embodiment, the linker comprises a hydrocarbon moiety attached to a cyclic disulfide. Suitable hydrocarbons are available commercially, and are attached to the cyclic disulfides. The hydrocarbon moiety is, in one aspect, a steroid residue. Oligonucleotide-nanoparticle conjugates prepared using linkers comprising a steroid residue attached to a cyclic disulfide are more stable to thiols compared to conjugates prepared using alkanethiols or acyclic disulfides as the linker, and in certain instances, the oligonucleotide-nanoparticle conjugates have been found to be 300 times more stable. In certain embodiments, the two sulfur atoms of the cyclic disulfide are close enough together so that both of the sulfur atoms attach simultaneously to the nanoparticle. In other aspects, the two sulfur atoms are adjacent each other. In aspects where utilized, the hydrocarbon moiety is large enough to present a hydrophobic surface screening the surfaces of the nanoparticle.

In other aspects, a method for attaching oligonucleotides onto a surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with enhanced stability and selectivity. The process comprises providing oligonucleotides, in one aspect, having covalently bound thereto a moiety comprising a functional group which can bind to the nanoparticles. The moieties and functional groups are those that allow for binding (i.e., by chemisorption or covalent bonding) of the oligonucleotides to nanoparticles. For example, oligonucleotides having an alkanethiol, an alkanedisulfide or a cyclic disulfide covalently bound to their 5' or 3' ends bind the oligonucleotides to a variety of nanoparticles, including gold nanoparticles.

Conjugates produced by use of the "aging" step have been found to be considerably more stable than those produced without the "aging" step. Increased density of the oligonucleotides on the surfaces of the nanoparticles is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. In certain aspects, the surface density is at least 15 picomoles/cm$^2$. Since the ability of the oligonucleotides of the conjugates to hybridize with nucleic acid and oligonucleotide targets can be diminished if the surface density is too great, the surface density is, in one aspect, no greater than about 35-40 picomoles/cm$^2$. Regardless, various oligonucleotide densities are contemplated as disclosed herein.

An "aging" step is incorporated into production of functionalized nanoparticles following an initial binding or oligonucleotides to a nanoparticle. In brief, the oligonucleotides are contacted with the nanoparticles in water for a time sufficient to allow at least some of the oligonucleotides to bind to the nanoparticles by means of the functional groups. Such times can be determined empirically. In one aspect, a time of about 12-24 hours is contemplated. Other suitable conditions for binding of the oligonucleotides can also be determined empirically. For example, a concentration of about 10-20 nM nanoparticles and incubation at room temperature is contemplated.

Next, at least one salt is added to the water to form a salt solution. The salt is any water-soluble salt, including, for example and without limitation, sodium chloride, magnesium chloride, potassium chloride, ammonium chloride, sodium acetate, ammonium acetate, a combination of two or more of these salts, or one of these salts in phosphate buffer. The salt is added as a concentrated solution, or in the alternative as a solid. In various embodiments, the salt is added all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time gives the highest surface density of oligonucleotides on the nanoparticles. Suitable ionic strengths can be determined empirically for each salt or combination of salts. In one aspect, a final concentration of sodium chloride of from about 0.1 M to about 1.0 M in phosphate buffer is utilized, with the concentration of sodium chloride being increased gradually over time.

After adding the salt, the oligonucleotides and nanoparticles are incubated in the salt solution for a period of time to allow additional oligonucleotides to bind to the nanoparticles to produce the stable nanoparticle-oligonucleotide conjugates. As will be described in detail below, an increased surface density of the oligonucleotides on the nanoparticles stabilizes the conjugates. The time of this incubation can be determined empirically. By way of example, in one aspect a total incubation time of about 24-48, wherein the salt concentration is increased gradually over this total time, is contemplated. This second period of incubation in the salt solution is referred to herein as the "aging" step. Other suitable conditions for this "aging" step can also be determined empirically. By way of example, an aging step is carried out with incubation at room temperature and pH 7.0.

The conjugates produced by use of the "aging" are in general more stable than those produced without the "aging" step. As noted above, this increased stability is due to the increased density of the oligonucleotides on the surfaces of the nanoparticles which is achieved by the "aging" step. The surface density achieved by the "aging" step will depend on the size and type of nanoparticles and on the length, sequence and concentration of the oligonucleotides.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

Oligonucleotide Density

Method are provided wherein the oligonucleotide is bound to the nanoparticle at a surface density of at least about 0.3 pmol/cm$^2$, at least about 0.6 pmol/cm$^2$, at least about 0.9 pmol/cm$^2$, at least about 1.2 pmol/cm$^2$, at least about 1.5 pmol/cm$^2$, at least about 1.8 pmol/cm$^2$, at least about 2.1 pmol/cm$^2$, at least about 2.4 pmol/cm$^2$, at least about 2.7 pmol/cm$^2$, at least about 3.0 pmol/cm$^2$, at least about 3.3 pmol/cm$^2$, at least about 3.6 pmol/cm$^2$, at least about 3.9 pmol/cm$^2$, at least about 4.2 pmol/cm$^2$, at least about 4.5 pmol/cm$^2$, at least about 4.8 pmol/cm$^2$, at least about 5.1 pmol/cm$^2$, at least about 5.4 pmol/cm$^2$, at least about 5.7 pmol/cm$^2$, at least about 6.0 pmol/cm$^2$, at least about 6.3 pmol/cm$^2$, at least about 6.6 pmol/cm$^2$, at least about 6.9 pmol/cm$^2$, at least about 7.2 pmol/cm$^2$, at least about 7.5 pmol/cm$^2$, at least about 7.8 pmol/cm$^2$, at least about 8.1 pmol/cm$^2$, at least about 8.4 pmol/cm$^2$, at least about 8.7 pmol/cm$^2$, at least about 9.0 pmol/cm$^2$, at least about 9.3 pmol/cm$^2$, at least about 9.6 pmol/cm$^2$, at least about 9.9 pmol/cm$^2$, at least 10 pmol/cm$^2$, at least 15 pmol/cm$^2$, at least 20 pmol/cm$^2$, at least 25 pmol/cm$^2$, at least 30 pmol/cm$^2$, at least 35 pmol/cm$^2$, at least 40 pmol/cm$^2$, at least 45 pmol/cm$^2$, at least 50 pmol/cm$^2$, or 50 pmol/cm$^2$ or more.

In one aspect, methods are provided wherein the packing density of the oligonucleotides on the surface of the nanoparticle is sufficient to result in cooperative behavior between nanoparticles. Methods include those wherein cooperative behavior between the nanoparticles increases the strength of the binding between the oligonucleotide and the target polynucleotide.

In another aspect, the cooperative behavior between the nanoparticles increases the resistance of the oligonucleotide to degradation, and/or increases the resistance of the oligonucleotide/polynucleotide complex to degradation. In certain aspects, cooperative behavior between the nanoparticles increases in the resistance of the oligonucleotides to degradation by a nuclease.

Methods also include those wherein the uptake of a nanoparticle of the invention can be modulated as a function of packing density of oligonucleotides on said nanoparticle. As shown herein, increasing oligonucleotide packing density on a first nanoparticle increases uptake of the nanoparticle compared to uptake of a second nanoparticle at a lower oligonucleotide packing density. Thus, in various aspects, the modulation of uptake may be either an increase or decrease in uptake. In still other aspects, the uptake of a first nanoparticle may be modulated at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 20-fold, at least 30-fold, at least 40-fold, at least 50-fold, or at least 100-fold or more compared to the uptake of a second nanoparticle having a packing density different from the first nanoparticle.

In one aspect, methods are contemplated in which one oligonucleotide is functionalized on a nanoparticle. In other aspects, 2, 3, 4, 5, 6, 7, 8, 9, 10, 11, 12, 13, 14, 15, 16, 17, 18, 19, or 20 oligonucleotides are functionalized on a nanoparticle. In still other aspects, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 85, at least 90, at least 95, at least 100 or more oligonucleotides are functionalized on a nanoparticle.

In one aspect, methods are contemplated wherein the packing density of the oligonucleotides on a first nanoparticle is increased by at least 1% compared to the packing density on a second nanoparticle. In other aspects, the packing density of the oligonucleotides on a first nanoparticle is increased by at least 2% compared to the packing density on a second nanoparticle. In still other aspects, the packing density of the oligonucleotides on a first nanoparticle is increased by at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 20-fold, at least 30-fold, at least 40-fold, at least 50-fold, or at least 100-fold or more compared to the packing density on a second nanoparticle.

In some aspects, increasing the packing density of oligonucleotides on a nanoparticle results in increasing numbers of proteins adsorbed to the oligonucleotide-functionalized nanoparticle. The proteins may originate from a number of sources, including but not limited to serum in cell culture medium, the extracellular matrix, cell-associated proteins, engineered proteins, cell-bound proteins, and circulating proteins. Without being bound by any theory or mechanism, the proteins may interact with the oligonucleotide-functionalized nanoparticle, and a higher number of oligonucleotides per nanoparticle results in a higher number of proteins adsorbed onto the oligonucleotide-functionalized nanoparticle, which in turn may allow for increased uptake of the nanoparticle compared to a nanoparticle having a lower number of oligonucleotides functionalized thereon.

In additional aspects, modulating the packing density of oligonucleotides on a nanoparticle is effected through the use of diluents. OEG is one such diluent that is useful due to its charge neutrality, water solubility, and its ability to passivate surfaces in a manner that resists adsorption of biological molecules (Prime et al., 1991 Science 252(5009): 1164-1167). In various aspects, diluent molecules are included in order to keep the Au NP surface fully passivated and the particles stable. In some aspects, the OEG diluent allows ASNPs to be synthesized with zero to 80±2 oligonucleotides per particle that are stable under all the conditions required for cell culture.

Oligonucleotide Copies—Same/Different Sequences

The term "oligonucleotide" includes those wherein a single sequence is attached to a nanoparticle, or multiple copies of the single sequence are attached. For example, in various aspects, an oligonucleotide is present in multiple copies in tandem, for example, two, three, four, five, six, seven eight, nine, ten or more tandem repeats.

Alternatively, the nanoparticle is functionalized to include at least two oligonucleotides having different sequences. As above, the different oligonucleotide sequences are in various aspects arranged in tandem and/or in multiple copies. Alternatively, the oligonucleotides having different sequences are attached directly to the nanoparticle. In methods wherein oligonucleotides having different sequences are attached to the nanoparticle, aspects of the methods include those wherein the different oligonucleotide sequences hybridize to different regions on the same polynucleotide. Alternatively, the different oligonucleotide sequences hybridize to different polynucleotides, thereby modulating gene expression from different target polynucleotides.

The oligonucleotides on the nanoparticles may all have the same sequence or may have different sequences that hybridize with different portions of the target polynucleotide. When oligonucleotides having different sequences are used, each nanoparticle may have all of the different oligonucleotides attached to it or the different oligonucleotides are attached to different nanoparticles. Alternatively, the oligonucleotides on each of the nanoparticles may have a plurality of different sequences, at least one of which must hybridize with a portion of the target polynucleotide.

In another aspect, multiple oligonucleotide are bound on a particle which allow for the ability to crosslink target polynucleotide via either inter- or intra-strand links. Crosslinking in this manner potentiates inhibition by various means including steric hindrance.

Spacers

In certain aspect, functionalized nanoparticles are contemplated which include those wherein an oligonucleotide is attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotide in tandem, whether the oligonucleotides have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, an ethylglycol, or combinations thereof.

In certain aspects, the spacer has a moiety covalently bound to it, the moiety comprising a functional group which can bind to the nanoparticles. These are the same moieties and functional groups as described above. As a result of the binding of the spacer to the nanoparticles, the oligonucleotide is spaced away from the surface of the nanoparticles and is more accessible for hybridization with its target. In instances wherein the spacer is a polynucleotide, the length of the spacer in various embodiments at least about 10 nucleotides, 10-30 nucleotides, or even greater than 30 nucleotides. The spacer may have any sequence which does not interfere with the ability of the oligonucleotides to become bound to the nanoparticles or to the target polynucleotide. The spacers should not have sequences complementary to each other or to that of the oligonucleotides, but may be all or in part complementary to the target polynucleotide. In certain aspects, the bases of the polynucleotide spacer are all adenines, all thymines, all cytidines, all guanines, all uracils, or all some other modified base.

In another embodiment, a non-nucleotide linker of the invention comprises a basic nucleotide, polyether, polyamine, polyamide, peptide, carbohydrate, lipid, polyhydrocarbon, or other polymeric compounds. Specific examples include those described by Seela and Kaiser, Nucleic Acids Res. 1990, 18:6353 and Nucleic Acids Res.

1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, the disclosures of which are all incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In various aspects, linkers contemplated include linear polymers (e.g., polyethylene glycol, polylysine, dextran, etc.), branched-chain polymers (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); lipids; cholesterol groups (such as a steroid); or carbohydrates or oligosaccharides. Other linkers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Other useful polymers as linkers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers.

In still other aspects, oligonucleotide such as poly-A or hydrophilic or amphiphilic polymers are contemplated as linkers, including, for example, amphiphiles (including oligonucletoides).

Types of Oligonucleotides. Including Modified Forms

In various aspects, methods include oligonucleotides which are DNA oligonucleotides, RNA oligonucleotides, or combinations of the two types. Modified forms of oligonucleotides are also contemplated which include those having at least one modified internucleotide linkage. In one embodiment, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization. The oligonucleotide incorporated with the universal base analogues is able to function as a probe in hybridization, as a primer in PCR and DNA sequencing. Examples of universal bases include but are not limited to 5'-nitroindole-2'-deoxyriboside, 3-nitropyrrole, inosine and pypoxanthine.

Modified Internucleoside Linkages

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide".

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

Modified Sugar and Internucleoside Linkages

In still other embodiments, oligonucleotide mimetics wherein both one or more sugar and/or one or more internucleotide linkage of the nucleotide units are replaced with "non-naturally occurring" groups. The bases of the oligonucleotide are maintained for hybridization with the target polynucleotide. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still other embodiments, oligonucleotides are provided with phosphorothioate backbones and oligonucleosides with heteroatom backbones, and including —CH$_2$—NH—O—CH$_2$—, —CH$_2$—N(CH$_3$)—O—CH$_2$—, —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligo consists of 2 to 4, desirably 3, groups/atoms selected from —CH$_2$—, —O—, —S—, —NR$^H$—, >C=O, >C=NR$^H$, >C—S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where RH is selected from hydrogen and C$_{1-4}$-alkyl, and R" is selected from C$_{1-6}$-alkyl and phenyl. Illustrative examples of such linkages are —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, O—CH$_2$—CH= (including R$^5$ when used as a linkage to a succeeding monomer), —CH$_2$—CH$_2$—O—, —NR$^H$—CH$_2$—CH$_2$—, —CH$_2$—CH$_2$—NR$^H$—, —CH$_2$—NR$^H$CH$_2$—, —O—CH$_2$—CH$_2$—NR$^H$—, —NR$^H$—CO—O—, —NR$^H$—CO—NR$^H$—, —NR$^H$—CS—NR$^H$—, —NR$^H$—C(=NR$^H$)—NR$^H$—, —NR$^H$—CO—CH$_2$—NR$^H$—O—CO—O, —O—CO—CH$_2$—O—, —O—CH$_2$—CO—O—, —CH$_2$—CO—NR$^H$—, —O—CO—NR$^H$—, —NR$^H$—CO—CH$_2$—, —O—CH$_2$—CO—NR$^H$—, —O—CH$_2$—CH$_2$—NR$^H$—, —CH=N—O—, —CH$_2$—NR$^H$—O—, —CH$_2$—O—N= (including R$^5$ when used as a linkage to a succeeding monomer), —CH$_2$—O—NR$^H$—, —CO—NR$^H$—CH$_2$—, —CH$_2$—NR$^H$—O—, —CH$_2$—NR$^H$—CO—, —O—NR$^H$—CH$_2$—, —O—NR$^H$, —O—CH$_2$—S—, —S—CH$_2$—O, —CH$_2$—CH$_2$—S—, —O—CH$_2$—CH$_2$—S—, —S—CH$_2$—CH= (including R$^5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$—CH$_2$—; —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —PO(BH$_3$)—O—, —O—PO(NHR$^N$)—O—, —O—P(O)$_2$—NR$^H$H—, —NR—P(O)$_2$—O—, —O—P(O,NR$^H$)—O—, —CH$_2$—P(O)$_2$—O—, —O—P(O)$_2$—CH$_2$—, and —O—Si(R")$_2$—O—; among which —CH$_2$—CO—NR$^H$—, —CH$_2$—NR$^H$—O—, —S—CH$_2$—O—, —O—P(O)$_2$—O—O—P(—O,S)—O—, —O—P(S)$_2$—O—, —NR$^H$(O)$_2$—O—, —O—P(O,NR$^H$)—O—, —O—PO(R")—O—, —O—PO(CH$_3$)—, and —O—PO(NHR$^N$)—O—, where RH is selected form hydrogen and C$_{1-4}$-alkyl, and R" is selected from C$_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. patent application NO. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH$_2$—)$_n$ group bridging the 2' oxygen atom and the 4' carbon atom wherein n is 1 or 2. LNAs and preparation thereof are described in WO 98/39352 and WO 99/14226.

Natural and Modified Bases

Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. 1., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyl-adenine, 7-deazaxanthine, 7-deazaguanine, $N^4,N^4$-ethano-cytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, Nucleic Acids Research, 1997, vol. 25, pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., Angewandte Chemie, International Edition, 1991, 30, 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Conjugates

Another modification of the oligonucleotides contemplated involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups contemplated include intercalators, reporter molecules, polyamines, polyamides, polyethylene glycols, polyethers, groups that enhance the pharmacodynamic properties of oligonucleotides, and groups that enhance the pharmacokinetic properties of oligonucleotides. Typical conjugate groups include cholesterols, lipids, phospholipids, biotin, phenazine, folate, phenanthridine, anthraquinone, acridine, fluoresceins, rhoda-mines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of the compounds of the present invention. Also contemplated are groups that enhance binding or association of the oligonucleotide or a targeting agent to its target (either the target polynucleotide of target of the targeting agent) by bringing either or both into proximity of the target through association or interaction with the actin/myosin intracellular framework, the early to late endosome framework, the translational to endoplasmic reticulum to golgi network pathway, etc.).

Representative conjugate groups are disclosed in International Patent Application PCT/US92/09196, filed Oct. 23, 1992, and U.S. Pat. No. 6,287,860, the entire disclosures of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glyc-ero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety. See, for example U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, the disclosures of which are incorporated herein by reference.

Still other conjugate moieties include proteins, peptides, and peptide mimetics. In one aspect, members from this group of moieties are selected based on their binding specificity to a ligand expressed in or on a target cell type or a target organ. Alternatively, moieties of this type include a receptor for a ligand on a target cell (instead of the ligand itself), and in still other aspects, both a receptor and its ligand are contemplated in those instances wherein a target cell expresses both the receptor and the ligand. In other aspects, members from this group are selected based on their biological activity, including for example enzymatic activity, agonist properties, antagonist properties, multimerization capacity (including homo-multimers and hetero-multimers). With regard to proteins, conjugate moieties contemplated include full length protein and fragments thereof which retain the desired property of the full length proteins. Fusion proteins, including fusion proteins wherein one fusion component is a fragment or a mimetic, are also contemplated. This group also includes antibodies along with fragments and derivatives thereof, including but not limited to Fab' fragments, F(ab)$_2$ fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

Chimerics

It is not necessary for all positions in a given compound to be uniformly modified, and in fact more than one of the aforementioned modifications may be incorporated in a single compound or even at a single nucleoside within an oligonucleotide. These "chimeric" antisense compounds typically contain at least one region including a modification as described herein, while the remainder of the oligonucleotide remains "unmodified."

In certain aspects, the modification confers increased resistance to nuclease degradation, increased cellular uptake, increased stability and/or increased binding affinity for the target nucleic acid. In other aspects the modification serves as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric compounds may be formed as composite structures of two or more oligonucleotides, modified oligonucleotides, oligonucleosides and/or oligonucleotide mimetics as described above. Such compounds have also been referred to in the art as hybrids or gapmers. See, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, the disclosures of which are incorporated herein by reference in their entireties.

Target Polynucleotides

In various aspects, the target polynucleotide is either eukaryotic, prokaryotic, or viral.

In various embodiments, methods provided include those wherein the target polynucleotide is a mRNA encoding a gene product and translation of the gene product is inhibited, or the target polynucleotide is DNA in a gene encoding a gene product and transcription of the gene product is inhibited. In methods wherein the target polynucleotide is DNA, the polynucleotide is in certain aspects DNA which encodes the gene product being inhibited. In other methods, the DNA is complementary to a coding region for the gene product. In still other aspects, the DNA encodes a regulatory element necessary for expression of the gene product. "Regulatory elements" include, but are not limited to enhancers, promoters, silencers, polyadenylation signals, regulatory protein binding elements, regulatory introns, ribosome entry sites, and the like. In still another aspect, the target polynucleotide is a sequence which is required for endogenous replication.

The terms "start codon region" and "translation initiation codon region" refer to a portion of an mRNA or gene that encompasses contiguous nucleotides in either direction (i.e., 5' or 3') from a translation initiation codon. Similarly, the terms "stop codon region" and "translation termination codon region" refer to a portion of such an mRNA or gene that encompasses contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the oligonucleotides on the functionalized nanoparticles.

Other target regions include the 5' untranslated region (5'UTR), the portion of an mRNA in the 5' direction from the translation initiation codon, including nucleotides between the 5' cap site and the translation initiation codon of an mRNA (or corresponding nucleotides on the gene), and the 3' untranslated region (3'UTR), the portion of an MRNA in the 3' direction from the translation termination codon, including nucleotides between the translation termination codon and 3' end of an MRNA (or corresponding nucleotides on the gene). The 5' cap site of an MRNA comprises an N7-methylated guanosine residue joined to the 5'-most residue of the MRNA via a 5'-5' triphosphate linkage. The 5' cap region of an MRNA is considered to include the 5' cap structure itself as well as the first 50 nucleotides adjacent to the cap site.

For prokaryotic target polynucleotides, in various aspects, the polynucleotide is genomic DNA or RNA transcribed from genomic DNA. For eukaryotic target polynucleotides, the polynucleotide is an animal polynucleotide, a plant polynucleotide, a fungal polynucleotide, including yeast polynucleotides. As above, the target polynucleotide is either a genomic DNA or RNA transcribed from a genomic DNA sequence. In certain aspects, the target polynucleotide is a mitochondrial polynucleotide. For viral target polynucleotides, the polynucleotide is viral genomic RNA, viral genomic DNA, or RNA transcribed from viral genomic DNA.

Desired Inhibition Results

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of an oligonucleotide-functionalized nanoparticle. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of nanoparticle and a specific oligonucleotide.

Kits

Also provided are kits for inhibiting gene expression from a target polynucleotide. In one embodiment, the kit comprises at least one container, the container holding at least one types of nanoparticles as described herein having one or more oligonucleotides as described here attached thereto. The oligonucleotides on the first type of nanoparticles have one or more sequences complementary (or sufficiently complementary as disclosed herein) to one or more sequences of a first portion of a target polynucleotide. The container optionally includes one or more additional type of nanoparticles which have a sequence complementary to one or more sequence of a second portion of the target polynucleotide.

In another embodiment, the kit comprises at least two containers. The first container holds one or more nanoparticles as disclosed herein having one or more oligonucleotides as described herein attached thereto which have a sequence complementary to one or more sequence of a portion of a target polynucleotide. The second container holds one or more nanoparticles having one or more oligonucleotides attached thereto which have a sequence complementary to one or more sequences of the same or a different portion of the target polynucleotide.

In another embodiment, the kits have oligonucleotides and nanoparticles in separate containers, and the oligonucleotides are to attached to the nanoparticles prior to use for inhibiting gene expression. In one aspect, the oligonucleotides and/or the nanoparticles are functionalized so that the oligonucleotides can be attached to the nanoparticles. Alternatively, the oligonucleotides and/or nanoparticles are provided in the kit without functional groups, in which case they must be functionalized prior to performing the assay.

In various aspects of the kits provided, oligonucleotides include a label or the kit includes a label which can be attached to the oligonucleotides. Alternatively, the kits include labeled nanoparticles or labels which can be attached to the nanoparticles. In each embodiment, the kit optionally includes instructions, each container contains a label, the kit itself includes a label, the kit optionally includes one or more non-specific oligonucleotides (either attached to nanoparticles or not attached to nanoparticles).

EXAMPLES

Example 1

Preparation of Gold Nanoparticles

Citrate-stabilized 13 nm gold nanoparticles were prepared by reduction of $HAuCl_4$ with citrate as described in Frens, Nature Phys. Sci., 241, 20 (1973) and Grabar, Anal. Chem., 67, 735 (1995). Briefly, all glassware was cleaned in aqua regia (3 parts HCl, 1 part HNO3), rinsed with Nanopure $H_2O$, then oven dried prior to use. $HAuCl_4$ and sodium citrate were purchased from Aldrich Chemical Company. An aqueous solution of $HAUCl_4$ (1 mM, 500 mL) was brought to a reflux while stirring, and then 50 mL of a 38.8 mM trisodium citrate solution was added quickly, resulting in a change in solution color from pale yellow to deep red. After the color change, the solution was refluxed for an additional fifteen minutes, allowed to cool to room temperature, and subsequently filtered through a Micron Separations Inc. 0.45 micron nylon filter. Au colloids were characterized by UV-vis spectroscopy using a Hewlett Packard 8452A diode array spectrophotometer and by Transmission Electron Microscopy (TEM) using a Hitachi 8100 transmission electron microscope. A solution of 13 nm diameter gold particles exhibits a characteristic surface plasmon band centered at 518-520 nm. that is useful in verifying the preparation of these particles.

Example 2

To probe the general uptake of antisense oligonucleotide-modified gold nanoparticle agents (ASNPs) in cells, a mouse cell line (C-166) and two human cancer models (HeLa and A594) were examined. These cell lines were chosen to represent different species and inherent differences between cell and tissue types. Sterile filtered ASNPs were added directly to the cell culture media of adherent cells in concentrations ranging from 1 to 60 nM. Forty-eight hours after nanoparticle addition, the cells were washed 3 times in PBS buffer, collected, and counted using a Guava EasyCyte flow cytometer (Guava Technologies). To prepare samples for inductively coupled plasma mass spectrometry (ICP-MS) (Thermo-Fisher), the cells were dissolved with neat nitric acid at 60° C. overnight. The Au content of the cell digest was determined by ICP-MS. Each cell sample was prepared in a matrix consisting of 3% $HNO_3$, 5 ppb Indium (internal standard), and Nanopure™ water. In order to extract the number of nanoparticles taken up by each cell, the number of nanoparticles must be calculated based on the concentration of Au found in the sample. This was done using the molecular weight of Au and the diameter of the nanoparticle to calculate Au atoms per particle ($6.78\times10^4$ atoms/particle). Once the number of particles was calculated, this particle number was divided by the cell count to determine the number of ASNPs per cell. Cell samples treated briefly (10 minutes) with ASNPs were prepared as above and used as controls for background subtraction in the case of ICP measurements to correct for any "sticking" of the nanoparticles to the cells and culture vessels during harvesting and preparation, or background ICP counts. All ICP experiments were performed in triplicate and values obtained were averaged. To test the validity of calculated nanoparticle values, we analyzed Au NP solutions with known concentrations (Ted Pella, Inc., 7×10$^{11}$ particles/mL, 1.16 nM). Gold samples were centrifuged (13,000 rpm, 30 min) and then re-suspended in 25 μL of KCN (0.1M) for 3 hours to completely dissolve the particles. Concentrations of 290 pM, 120 pM, 29 pM, 12 pM, 4.6 pM, 1.8 pM, 500 fM, were analyzed by ICP-MS. Calculated values were similar to manufacturer concentrations (22.1% standard error). The results of these experiments demonstrate that while the uptake of ASNPs is universal across multiple cell types, the absolute number of nanoparticles varies by cell type by as much as a factor of 20 (FIG. 1).

The amount of ASNPs found in each cell is proportional to the concentration of particles added to the media over the range of concentrations tested. Specifically, at low concentrations uptake varies by concentration in a linear manner, until a saturation point is reached at the highest concentrations tested (FIG. 1). Additionally, the total number of ASNPs determined to enter or associate with each cell type is remarkably high, reaching up to 3×10$^7$ nanoparticles per cell in C166 cells. Similarly, the maximum number of ASNPs is 1×10$^7$ and 1×10$^6$ nanoparticles per cell in HeLa and A549 cells, respectively. For comparison purposes, others have observed from one thousand to five thousand nanoparticles per cell in an analogous cell-line for Au NPs that are not functionalized with DNA (Chithrani et al., 2007, Nano Lett. 7(6): 1542-1550). These experiments used a similar collection, washing, and mass-based quantification process, and underscore the importance of oligonucleotide functionalization.

Example 3

Figure 2:
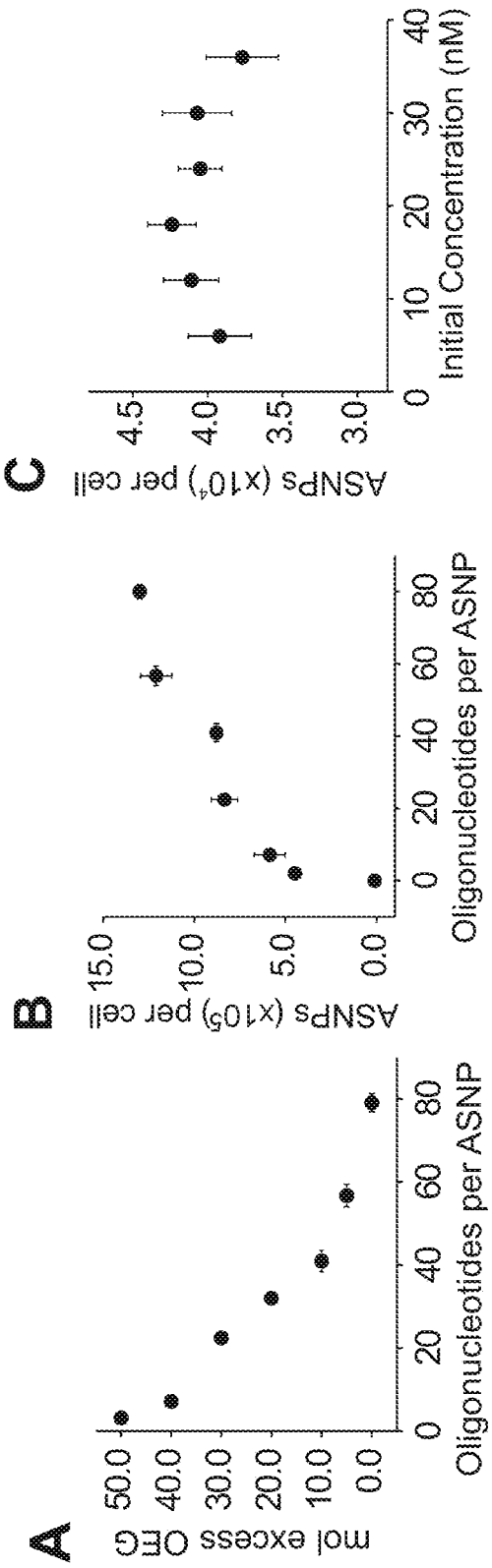
FIG. 2. A) Characterization of oligonucleotide loading on OEG (oligo(ethylene glycol)):DNA particles. B) Uptake as a function of the number of oligonucleotides per ASNP in A549 cells. C) Au NPs functionalized with OEG show comparatively little uptake (A549 cells) even at high concentration additions.

Since the number of ASNPs associated with each cell was found to be higher than reported values for other modified Au NP systems, it was hypothesized that the oligonucleotides were strongly contributing to cellular uptake. To probe this contribution, particles with varying numbers of oligonucleotides were prepared by co-functionalizing them with OEG thiol diluent (FIG. 2A). OEG was chosen due to its charge neutrality, water solubility, and its ability to passivate surfaces in a manner that resists adsorption of biological molecules (Prime et al., 1991 Science 252(5009): 1164-1167). It should be noted that diluent molecules must be included in order to keep the Au NP surface fully passivated and the particles stable. This OEG diluent allowed ASNPs to be synthesized with zero to 80±2 oligonucleotides per particle that were stable under all the conditions required for cell culture. The stoichiometry during the functionalization process was varied to produce a range of DNA loadings (FIG. 2A).

Quantification of the cellular uptake of these mixed monolayer particles demonstrated that these values are highly dependent on the number of oligonucleotides immobilized on each ASNP. For example, with the A549 cell line (FIG. 2B), which is qualitatively representative of the behavior of the C166 and HeLa cells, particles with lower oligonucleotide loadings are not readily internalized by cells. However, at loadings of 60 strands per particle cellular association reaches a maximum of approximately 1.3×10$^6$ ASNPs/cell, and does not appreciably increase at higher oligonucleotide density. For comparison purposes, OEG-functionalized particles without oligonucleotides were also prepared and investigated under identical experimental conditions. While still exhibiting uptake, (thousands of nanoparticles per cell) even at the highest (36 nM) concentrations examined, the uptake of fully OEG-functionalized particles were significantly lower than the ASNP particles (10$^3$ lower uptake) (FIG. 2C).

In addition to quantitative measurements, we also investigated the size and surface potential of the particles before and after exposure to cell culture conditions to gain insight into how they were interacting with the extracellular environment. Dynamic light scattering (DLS) measurements were performed to estimate the initial measured hydrodynamic radius of the ASNPs. DLS data show that the average diameter of an ASNP functionalized with only DNA (approximately 80 strands; 13 nm Au NP) is 42±1 nm while that of a fully OEG-functionalized particle is 27±1 nm. Interestingly, the average size of the DNA-functionalized particles increases to 76±3 nm upon exposure to cell culture media, while the size of the OEG functionalized particle remains relatively constant (Table 1). This observation suggests that in cell culture media alone, some components are attracted to the ASNPs, which results in an increase in size.

TABLE 1

ASNP characteristics before and after media exposure.

| Oligonucleotide Strands/AuNP | Diameter (nm) | | Surface potential (mV) | | Adsorbed proteins/ ASNP |
| --- | --- | --- | --- | --- | --- |
| | before media | after media | before media | after media | |
| 79 ± 2 | 42 ± 1 | 76 ± 3 | −21 ± 4 | −13 ± 1 | 23 ± 3 |
| 32 ± 1 | 56 ± 2 | 77 ± 2 | −36 ± 2 | −24 ± 2 | 14 ± 1 |
| 7 ± 1 | 38 ± 1 | 50 ± 2 | −34 ± 2 | −27 ± 1 | 10 ± 1 |
| 0 | 27 ± 1 | 30 ± 1 | −20 ± 1 | −19 ± 1 | 2 ± 3 |

Zeta potential measurements indicate a change in surface potential that accompanies the size change of the ASNP, which we hypothesize is due to positively charged serum proteins binding to the DNA shell on the Au NPs (Table 1). Initially, the surface potential of the ASNPs in non-serum containing media was −21±4 mV. After exposure to media containing proteins, the ASNPs became more positively charged at −13±1 mV. In contrast, Au NPs functionalized with OEG did not show a change in surface potential after exposure to serum containing media. While ASNPs appear to become associated with serum proteins, the OEG particles do not. This is consistent with the well-characterized passivation properties of OEG monolayers with respect to protein adsorption (Prime et al., 1991 Science 252(5009): 1164-1167).

Further analysis using a fluorescence-based assay for protein quantification was carried out and confirmed that the observed size and surface potential changes were due to protein adsorption on the ASNP surface. Additionally, this assay allowed for an estimate of the number of proteins that are attached to each particle. ASNPs (final concentration 6 nM) were incubated both in serum-containing media and serum-free media for 24 hrs at 37° C. After this treatment, ASNPs were isolated from solution via three consecutive centrifugation steps (13,000 rpm, 20 mnn), and washed with PBS buffer to remove unbound proteins, and finally the Au NPs were dissolved with KCN (2.5 mM final concentration). A Quant-iT fluorescence protein assay (Invitrogen) was used to determine the relative number of proteins in the solution. Estimation of the number of bound proteins per ASNP was calculated using a standard curve and an assumed average protein size of 60 kD. In the case of a fully DNA-functionalized Au NP (80 strands per 13 nm particle), approximately 23 proteins remain attached to each particle after separation from the media (assuming an average protein is 60 kD). As the number of oligonucleotides per particle decreases, so does the number of proteins per particle (Table 1). These numbers may be interpreted as minimum values, as the washing process to remove unbound proteins could remove weakly bound proteins from the ASNPs. Nonetheless, the assay allows for comparison of particles functionalized with varying numbers of oligonucleotides, and it confirms that the density of oligonucleotides directly correlates with the number of proteins, providing one possible reason for the increasing numbers of ASNPs as a function of the DNA loading in the case of particles exposed to cell culture media. While others have looked at the contribution of non-specific serum proteins to the uptake of citrate stabilized Au NPs (Chithrani et al., 2006 Nano Letters 6(4): 662-668), the number of proteins as a determining factor in the uptake of Au NPs has not yet been established. Data presented herein show that specific surface modification by oligonucleotides can be used to control the number of proteins and hence control cellular interactions of Au NP agents and perhaps materials in general. The measurements demonstrate that the quantity of ASNPs associated with each cell is significant, and orders of magnitude larger than what has been observed for non-functionalized, protein or peptide-modified Au NPs (Liu et al., 2007 Analytical Chemistry 79(6): 2221-2229).

In summary, based on literature precedent and the negative charge presented by the DNA functionalization, this uptake ability would not be anticipated. To test the contribution of the oligonucleotides present on the nanoparticle surface to their cellular uptake, the density of oligonucleotides on the surface was varied using OEG as a diluent. Even at high concentrations, it was found that Au NPs functionalized with only OEG showed comparatively little internalization by the cell models studied. The data indicate that the number of proteins increases with the number of oligonucleotides on the surface, reaching a maximum of 23 proteins/particle. Further, their subsequent uptake correlates well with the number of absorbed proteins. The uptake plateau at 60 oligonucleotides per particle is perhaps due to a saturation of proteins on the surface of the oligonucleotide layer. Beyond this point, additional oligonucleotides may confer no additional ability to recruit proteins. Compared to other particles and traditional transfection agents, the differences in uptake of ASNPs may be due to both the number and nature of the proteins which are attracted to the oligonucleotides on the ASNPs.

Thus, in the co-functionalized particles the oligonucleotides provide the contribution to cellular internalization. By increasing the number of oligonucleotides, increased uptake of the ASNPs was observed, with a maximum uptake reached at loadings of approximately 60 oligonucleotides per Au NP. These data show that the surface density of oligonucleotides mediate the amount of nanoparticles internalized by cells.

Example 4

Figure 3:
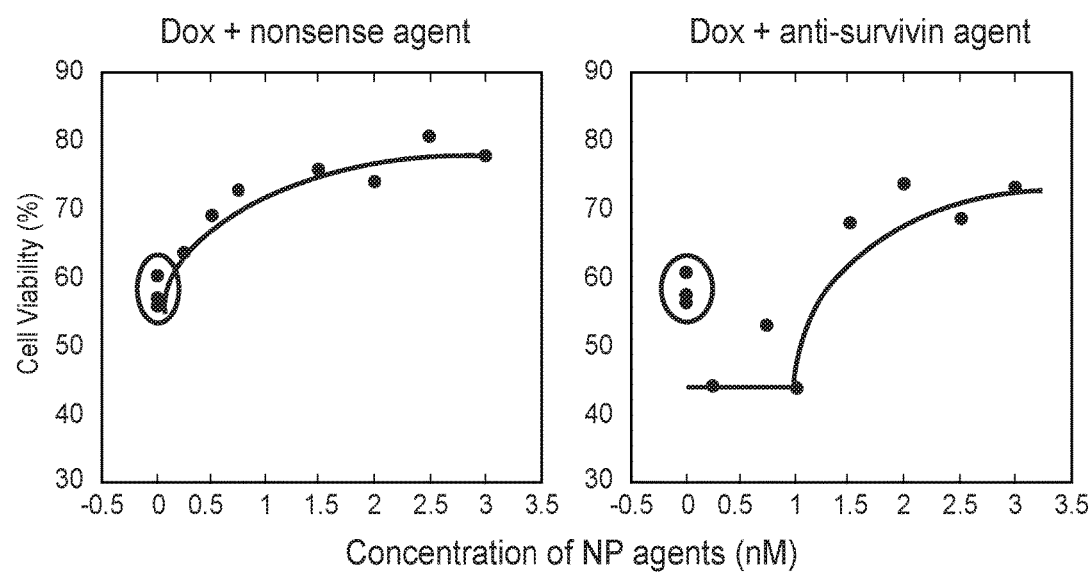
FIG. 3. Plots of cell viability as a function of nanoparticle concentration of dox-treated cell cultures. Dox-treated controls are circled. The lines are drawn as a guide to the eye.

As proof of the oligonucleotide-modified gold nanoparticle for drug control concept, the anticancer drug doxorubicin hydrochloride (dox) in a lung cancer cell model (A549) was investigated. Cultures treated with dox-containing cell culture media were observed that displayed a significant decrease in cell viability (cells are approximately 60% viable at 25 μm dox concentration) as a result of the systemic toxicity of this anticancer drug. However, when an oligonucleotide functionalized nanoparticle agent containing a non-specific sequence is added to the culture at the same point as the drug molecule, a dose-dependant recovery of cell viability is observed (cells recover to approximately 80% viable at 3 nM concentration of nanoparticles). The dox-treated cells were then examined in the presence of an anti-survivin oligonucleotide modified gold nanoparticle conjugate. Anti-survivin oligonucleotides have been shown to sensitize cells to chemotherapeutic agents. In these studies, the anti-survivin containing nanoparticle agent added to the culture at the same point as the drug molecule reduce cell viability to 45% at low concentrations and recover cell viability to 75% at high concentrations (FIG. 3). These examples demonstrate that oligonucleotide-modified nanoparticles can be used to control the efficacy of delivered drugs.

These experiments demonstrate that oligonucleotide-modified nanoparticle agents can be used to modulate drug effects. In the case of a nonspecific oligonucleotide modified nanoparticle agent, the agent interacts strongly with the drug molecule, and alters the normal mechanism by which the drug enters the cells. In the case of the anti-survivin oligonucleotide modified nanoparticle agent, it is probable that the agent interacts with the drug molecules at high concentrations. At low particle agent concentrations however, excess dox weakens the cell, and anti-survivin particles make the drug more effective.

Example 5

To probe the intracellular distribution of the dox, confocal fluorescence imaging experiments were carried out to visualize the fluorescent dox molecules in the cells. Imaging studies indicate that oligonucleotide-modified nanoparticles change the cellular-distribution of dox. Cells treated with dox alone have the majority of the fluorescent drug molecule in their nucleus, while cells treated with dox and a high concentration of nanoparticles have more cytoplasmic localization of the drug molecules. These experiments provide insight into the mechanism that reduces the toxic affects of this drug at high nanoparticle concentrations.

Numerous modifications and variations in the invention as set forth in the above illustrative examples are expected to occur to those skilled in the art. Consequently only such limitations as appear in the appended claims should be placed on the invention.

What is claimed is:

1. A method of modulating effectiveness of an anticancer drug comprising the step of:
administering said anticancer drug concomitantly with an oligonucleotide-functionalized nanoparticle, wherein said oligonucleotide-functionalized nanoparticle comprises an oligonucleotide comprising a sequence that modulates the effectiveness of said anticancer drug, and wherein the nanoparticle does not comprise a targeting agent.

2. The method of claim 1 wherein cellular localization of the anticancer drug is controlled by the oligonucleotide-functionalized nanoparticle.

3. The method of claim 1 wherein the oligonucleotide sequence is a chemosensitizing antisense sequence.

4. The method of claim 3 wherein the chemosensitizing antisense sequence increases the toxicity of the anticancer drug.

5. The method of claim 1 wherein the nanoparticle is non-metallic.

6. The method of claim 1 wherein the nanoparticle is metallic.

7. The method of claim 6 wherein the nanoparticle comprises gold, silver, platinum, aluminum, palladium, copper, cobalt, indium, or nickel.

8. The method of claim 1 wherein the effectiveness of the anticancer drug is altered by at least 10%, or at least 15%, or at least 20%, or at least 25%, or at least 30%, or at least 40%, or at least 50%, or at least 60%, or at least 70%, at least 80%, at least 90%, at least 95%, at least 2-fold, at least 5-fold, at least 10-fold, at least 20-fold, at least 50-fold or more compared to effectiveness of the anticancer drug in the absence of the oligonucleotide-functionalized nanoparticle.

9. The method of claim 1 wherein the oligonucleotide is from about 5 to about 100 nucleotides in length.

10. The method of claim 1 wherein the nanoparticle is from about 5 nanometers (nm) to about 50 nm in mean diameter.

11. The method of claim 1 wherein at least 20 oligonucleotides are functionalized to the nanoparticle.

12. The method of claim 1 wherein density of oligonucleotide on the surface of the nanoparticle is from about 1.5 pmol/cm$^2$ to about 25 pmol/cm$^2$.

13. The method of claim 1 wherein density of oligonucleotide on the surface of the nanoparticle is about 4 pmol/cm$^2$.

14. The method of claim 1 wherein the oligonucleotide is attached to the nanoparticle through a spacer.

15. The method of claim 1 wherein the oligonucleotide is a DNA oligonucleotide or a RNA oligonucleotide.

16. The method of claim 1 wherein the oligonucleotide-functionalized nanoparticle is associated with the anticancer drug.

* * * * *

UNITED STATES PATENT AND TRADEMARK OFFICE
CERTIFICATE OF CORRECTION

PATENT NO. : 10,370,656 B2
APPLICATION NO. : 15/296387
DATED : August 6, 2019
INVENTOR(S) : Chad A. Mirkin et al.

It is certified that error appears in the above-identified patent and that said Letters Patent is hereby corrected as shown below:

In the Specification

At Column 1, Line 19:
"This invention was made with government support under Grant Nos. 1 U54 CA119341-01 and U54 CA119341-02 awarded by The National Cancer Institute (NCI)/Centers of Cancer Nanotechnology Excellence (CCNE) and Grant Nos. 5 DPI OD000285-02 and DPI OD000285, awarded by the National Institute of Health (NIH Pioneer Award). The government has certain rights in the invention."

Should read:
"This invention was made with government support under grant numbers U54 CA119341 and OD000285 awarded by the National Institutes of Health. The government has certain rights in the invention."

Signed and Sealed this
Third Day of May, 2022

Katherine Kelly Vidal
*Director of the United States Patent and Trademark Office*